United States Patent
Ijzermann et al.

(10) Patent No.: US 7,781,432 B2
(45) Date of Patent: Aug. 24, 2010

(54) ANALOGS OF NITROBENZYLTHIOINOSINE

(75) Inventors: Adriaan Pieter Ijzermann, Haarlem (NL); Reynier Tromp, Leiden (NL)

(73) Assignees: Gruenenthal GmbH, Aachen (DE); Leiden University, Leiden (NL)

( * ) Notice: Subject to any disclaimer, the term of this patent is extended or adjusted under 35 U.S.C. 154(b) by 649 days.

(21) Appl. No.: 11/647,222

(22) Filed: Dec. 29, 2006

(65) Prior Publication Data
US 2007/0197528 A1  Aug. 23, 2007

Related U.S. Application Data

(63) Continuation of application No. PCT/EP2005/006883, filed on Jun. 27, 2005.

(30) Foreign Application Priority Data

Jun. 29, 2004 (EP) .................................. 04015195

(51) Int. Cl.
C07D 473/24 (2006.01)
A61K 31/52 (2006.01)
A61P 25/04 (2006.01)

(52) U.S. Cl. ............ 514/234.2; 514/263.2; 514/263.37; 514/45; 544/118; 544/276; 536/27.8

(58) Field of Classification Search .................. 514/45, 514/234.2, 263.2, 263.37; 544/118, 276; 536/27.8
See application file for complete search history.

(56) References Cited

U.S. PATENT DOCUMENTS

| 3,085,121 | A | * | 4/1963 | Guest et al. | 585/357 |
| 3,461,098 | A | * | 8/1969 | Apel et al. | 528/196 |
| 5,017,701 | A | * | 5/1991 | Grinter et al. | 544/276 |
| 5,965,563 | A | * | 10/1999 | Buzzetti et al. | 514/263.2 |
| 6,958,344 | B2 | * | 10/2005 | Bonnert et al. | 514/263.37 |
| 7,358,235 | B2 | * | 4/2008 | Puetz et al. | 514/45 |
| 2003/0187261 | A1 | * | 10/2003 | Havlicek et al. | 544/276 |

OTHER PUBLICATIONS

Brajeswar Paul, Marianne F. Chen, Alan R. P. Paterson J. Med. Chem., 1975, 18 (10), pp. 968-973.*

Tromp et al, J. Med. Chem., 2004, 47 (22), pp. 5441-5450.*

Weisner, The Journal of Pharmacology and Experimental Therapeutics vol. 289, Issue 3, 1669-1677, Jun. 1999.*

"Phenyl group" <http://en.wikipedia.org/wiki/Phenyl_group> dowlloaded from the internet Dec. 11, 2009.*

Abstract of Malhotra et al., *Effect of adenosine receptor modulation on pentylenetetrazole-induced seizures in rats*, British Journal of Pharmacology, vol. 120, pp. 282-288 (1997).

Gerritt P. Bean, Application of Natural Bond Orbital Analysis and Natural Resonance Theory to Delocalization and Aromaticity in Five-Membered Heteroaromatic Compounds, *Journal of Organic Chemistry*, 63:2497-506 (1998).

* cited by examiner

Primary Examiner—Mark L Berch
(74) *Attorney, Agent, or Firm*—Crowell & Moring LLP

(57) ABSTRACT

Analogs or derivatives of nitrobenzylthioinosine corresponding to formula I:

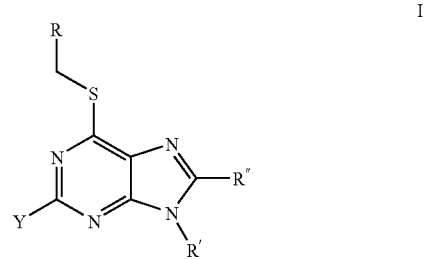

in which R represents an unsubstituted or mono- or polysubstituted phenyl, benzyl or heteroaryl group or a phenyl group condensed with heteroaryl, and R" represents an unsubstituted or mono- or polysubstituted NH—$C_{1-6}$-alkyl, NH-aryl, NH-heteroaryl, NH—$C_{3-8}$-cycloalkyl, NH—$C_{1-3}$-alkyl-aryl, NH—$C_{1-3}$-alkyl-heteroaryl, N($C_{1-6}$-alkyl)$_2$, N($C_{1-3}$-alkyl-aryl)$_2$, N($C_{1-3}$-alkyl-heteroaryl)$_2$, piperidine, piperazine, morpholine or pyrrolidine group; pharmaceutical compositions comprising such analogs or derivatives, and the use of such analogs or derivatives for treating pain and/or various other diseases.

15 Claims, No Drawings

ANALOGS OF NITROBENZYLTHIOINOSINE

CROSS REFERENCE TO RELATED APPLICATIONS

This application is a continuation of international patent application no. PCT/EP2005/006883, filed Jun. 27, 2005 designating the United States of America, and published in English on Jan. 12, 2006 as WO 2006/002846, the entire disclosure of which is incorporated herein by reference. Priority is claimed based on European patent application no. EP 04015195.3, filed Jun. 29, 2004.

BACKGROUND OF THE INVENTION

The present invention relates to new analogs or derivatives of nitrobenzylthioinosine, to pharmaceutical compositions comprising such new analogs or derivatives of nitrobenzylthioinosine, and to the use such analogs or derivatives of nitrobenzylthioinosine for the treatment of pain and various other diseases.

The treatment of pain conditions is of great importance in medicine. There is currently a world-wide need for additional pain therapy. The pressing requirement for a target-oriented treatment of pain conditions which is right for the patient, which is to be understood as the successful and satisfactory treatment of pain for the patients, is documented in the large number of scientific works which have recently and over the years appeared in the field of applied analgesics or on basic research on nociception.

The facilitated, carrier-mediated transport of nucleosides across mammalian cell membranes can be inhibited by a number of ligands including nucleoside derivatives such as nitrobenzylthioinosine (NBTI)

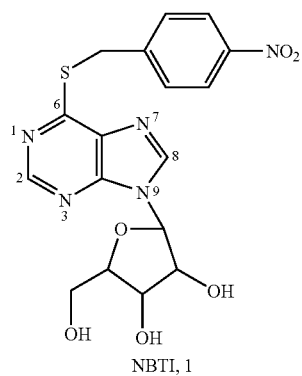

NBTI, 1 and non-nucleoside compounds including marketed substances such as dipyridamole and dilazep. Such compounds contribute to the physiological actions of adenosine. Through their blockade of the transport protein they increase the extracellular concentration of adenosine. This increase in adenosine levels causes a more profound occupancy of adenosine receptors through which adenosine exerts many of its physiological effects. The high hydrophilicity of NBTI and other transport inhibitors, however, may hinder their penetration into the central nervous system (CNS), where adenosine is involved in e.g., counteracting neuropathic pain.

An earlier study indicated that a nitro group, preferably at the 4-position of the benzyl moiety in NBTI, is a prime factor in determining the potency of inhibition of nucleoside transport in human erythrocytes (Paul, B.; Chen, M. F.; Paterson, A. R. P. *J. Med. Chem.* 1975, 18, 968-973; Baldwin, S. A.; Mackey, J. R.; Cass, C. E.; Young, J. D. *Molecular Medicine Today* 1999, 5, 216-224).

Despite the efforts of the art, there has remained a need for new compounds and pharmaceutical compositions which can be used for the effective treatment of pain as well as other conditions.

SUMMARY OF THE INVENTION

Accordingly, it was an object of the present invention to provide new substances useful in the treatment of pain.

Another object was to provide new substances which could be used to treat indications other than pain, such as Still another object was to provide pharmaceutical compositions incorporating such substances.

A further object of the present invention was to provide substances with reduced polarity while maintaining substantial affinity for the transport protein.

To gain further information on the interaction of NBTI with the nucleoside transporter-associated binding site the present inventors systematically replaced a number of substituents at C6, C8 and N9.

It has now been found that new derivatives of nitrobenzylthioinosine are surprisingly useful in the treatment of pain but also other indications.

The invention thus relates to a nitrobenzylthioinosine compound corresponding to formula I:

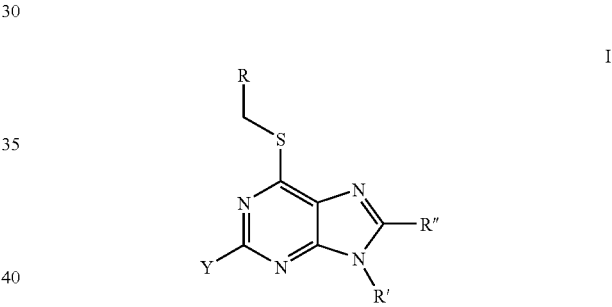

wherein

Y is selected from the group consisting of H, OH, SH, F, Cl, Br, I, —CF$_3$, —CHF$_2$, —CH$_2$F, —OCH$_3$, —OC$_2$H$_5$, —CH$_3$ and —C$_2$H$_5$;

R is selected from the group consisting of phenyl, benzyl, heteroaryl, and phenyl condensed with a heteroaryl, each mono- or polysubstituted or unsubstituted respectively;

R' is selected from ribose, mono- or polysubstituted, C$_{1-6}$-alkyl saturated or unsaturated, mono- or polysubstituted or unsubstituted; C$_{3-8}$-cycloalkyl or C$_{3-8}$-cycloalkyl containing 1 or 2 heteroatoms selected from S, O or N in the ring, mono- or polysubstituted or unsubstituted respectively; phenyl or benzyl, mono- or polysubstituted or unsubstituted respectively; or C$_{1-6}$-alkyl-O—R''', wherein alkyl may be saturated or unsaturated, and mono- or polysubstituted or unsubstituted, and R''' is selected from phenyl, heteroaryl, C$_{3-8}$-cycloalkyl, and C$_{3-8}$-cycloalkyl containing 1 or 2 heteroatoms selected from S, O and N in the ring; each mono- or polysubstituted or unsubstituted, respectively;

R'' is selected from NH—C$_{1-6}$-alkyl, NH-aryl, NH-heteroaryl, NH—C$_{3-8}$-cycloalkyl, NH—C$_{1-3}$-alkyl-aryl, NH—C$_{1-3}$-alkyl-heteroaryl, N(C$_{1-6}$-alkyl)$_2$, N(C$_{1-3}$-alkyl-aryl)$_2$, N(C$_{1-3}$-alkyl-heteroaryl)$_2$, piperidine, piperazine, morpholine and pyrrolidine, each unsubstituted or mono- or polysubstituted, respectively, optionally in the form of its racemate, pure stereoisomers, especially enantiomers or diastereomers, or in the form of mixtures of stereoisomers, especially enantiomers or diastereomers, in any suitable ratio; and/or in the form shown or in form of the acid or base or in form of a salt, especially a physiologically compatible salt, or in form of a solvate, especially a hydrate.

These derivatives of nitrobenzylthioinosine are surprisingly effective in the treatment of pain and in other indications. Inhibitors of nucleoside transport have a potential as drugs enhancing adenosine's actions in the CNS. As such their use is in the treatment of chronic and/or neuropathic pain, epilepsy and other CNS-related disorders. Currently available ligands are often very hydrophilic, preventing substantial passage of the blood-brain barrier. In this invention the derivatives according to the invention show decreased hydrophilicity. Many compounds proved to have affinities in the nanomolar range with the substantial reduction in polarity achieved being promising to have more favorable characteristics in aspects of absorption and distribution.

In the sense of this invention the terms alkyl- or cykloalkyl mean saturated or unsaturated (but not aromatic), branched, unbranched and cyclic carbohydrates that are unsubstituted monosubstituted or polysubstituted. $C_{1-2}$-alkyl denominates C1- or C2-alkyl; $C_{1-3}$-alkyl C1-, C2- or C3-alkyl; $C_{1-4}$-alkyl C1-, C2-, C3- or C4-alkyl; $C_{1-5}$-alkyl C1-, C2-, C3-, C4- or C5-alkyl; $C_{1-6}$-alkyl C1-, C2-, C3-, C4-, C5- or C6-alkyl; $C_{1-7}$-alkyl C1-, C2-, C3-, C4-, C5-, C6- or C7-alkyl; $C_{1-8}$-alkyl C1-, C2-, C3-, C4-, C5-, C6-, C7- or C8-alkyl; $C_{1-10}$-alkyl C1-, C2-, C3-, C4-, C5-, C6-, C7-, C8-, C9- or C10-alkyl; and $C_{1-18}$-alkyl C1-, C2-, C3-, C4-, C5-, C6-, C7-, C8-, C9-, C10-, C11-, C12-, C13-, C14-, C15-, C16-, C17- oder C18-alkyl. Further $C_{3-4}$-cycloalkyl denominates C3- or C4-cycloalkyl; $C_{3-5}$-cycloalkyl C3-, C4- or C5-cycloalkyl; $C_{3-6}$-cycloalkyl C3-, C4-, C5- or C6-cycloalkyl; $C_{3-7}$-cycloalkyl C3-, C4-, C5-, C6- or C7-cycloalkyl; $C_{3-8}$-cycloalkyl C3-, C4-, C5, C6-, C7- or C8-cycloalkyl; $C_{4-5}$-cycloalkyl C4- or C5-cycloalkyl; $C_{4-6}$-cycloalkyl C4-, C5- or C6-cycloalkyl; $C_{4-7}$-cycloalkyl C4-, C5-, C6- or C7-cycloalkyl; $C_{5-6}$-cycloalkyl C5- or C6-cycloalkyl; and $C_{5-7}$-cycloalkyl C5-, C6- oder C7-cycloalkyl. In regard to cycloalkyl cycloalkyl covers also saturated cycloalkyls, in which 1 or 2 carbonatoms are substituted by a heteroatom, S, N oder O. Cycloalkyl also covers once or multi unsaturated residues as long as cycloalkyl does not represent an aromatic system. Preferably alkyl or cycloalkyl methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, adamantyl, $CHF_2$, $CF_3$, $CH_2OH$, pyrazolinone, oxopyrazolinon, [1,4] dioxane or dioxolane.

In connection with alkyl and cycloalkyl, if not defined otherwise, the term "substituted" within the context of the present invention is understood to mean the replacement of an hydrogen atom by F, Cl, Br, I, $NH_2$, SH or OH, and the expression "polysubstituted" radicals is understood to mean that the substitution takes place multiply with the same or different substituents on different as well as on the same atoms, for example triple substitution on the same C atom as in the case of $CF_3$ or at different positions as in the case of —CH(OH)—CH=CH—$CHCl_2$. Particularly preferred substituents in this connection are F, Cl and OH.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, and the term $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$—, etc.

The term aryl radical is understood to mean ring systems with at least one aromatic ring but without heteroatoms in also only one of the rings. Examples are phenyl, naphthyl, fluoranthenyl, fluorenyl, tetralinyl or indanyl, in particular 9H-fluorenyl or anthracenyl radicals, which may be unsubstituted or singly or multiply substituted.

The term heteroaryl radical is understood to mean heterocyclic ring systems with at least one unsaturated ring, which contain one or more heteroatoms from the group comprising nitrogen, oxygen and/or sulfur, and which may also be singly or multiply substituted. Examples of the group of heteroaryls that may be mentioned include furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole, indole and quinazoline.

In this connection the term substituted in connection with aryl and heteroaryl is understood to denote the substitution of the aryl or heteroaryl with $R^{23}$, $OR^{23}$, a halogen, preferably F and/or Cl, a $CF_3$, a CN, an $NO_2$, an $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene. In this connection the radical $R^{23}$ denotes H, a $C_{1-10}$-alkyl radical, preferably a $C_{1-6}$-alkyl radical, an aryl or heteroaryl radical or an aryl or heteroaryl radical bonded via a $C_{1-3}$-alkylene group, wherein these aryl and heteroaryl radicals may not themselves be substituted by aryl or heteroaryl radicals. The radicals $R^{24}$ and $R^{25}$, which are identical or different, denote H, a $C_{1-10}$-alkyl radical, preferably a $C_{1-6}$-alkyl radical, an aryl radical, a heteroaryl radical or an aryl or heteroaryl radical bonded via a $C_{1-3}$-alkylene group, wherein these aryl and heteroaryl radicals may not themselves be substituted by aryl or heteroaryl radicals, or the radicals $R^{24}$ and $R^{25}$ together denote $CH_2CH_2OCH_2CH_2$, $CH_2CH_2NR^{26}CH_2CH_2$, or $(CH_2)_{3-6}$. The radical $R^{26}$ denotes H, a $C_{1-10}$-alky radical, preferably a $C_{1-6}$-alkyl radical, an aryl or heteroaryl radical, or an aryl or heteroaryl radical bonded via a $C_{1-3}$-alkylene group, wherein these aryl and heteroaryl radicals may not themselves be substituted with aryl or heteroaryl radicals.

The term salt is understood to mean any form of the active constituent according to the invention in which this adopts an ionic form or is charged and is coupled to a counterion (a cation or anion), and is present in solution. The term is also understood to include complexes of the active constituent with other molecules and ions, in particular complexes that are complexed via ionic interactions.

The term physiologically compatible salt with cations or bases is understood within the context of the present invention to mean salts of at least one of the compounds according to the invention—generally of a (deprotonated) acid—as an anion of at least one, preferably inorganic cation, that are physiologically compatible, especially when used in humans and/ or mammals. Particularly preferred are the salts of alkali and alkaline earth metals, but also with $NH_4^+$, and in particular (mono) or (di)sodium, (mono) or (di)potassium, magnesium or calcium salts.

The term physiologically compatible salt with anions or acids is understood within the context of the present invention to mean a salt of at least one of the compounds according to the invention—generally protonated, for example on the nitrogen atom—as a cation with at least one anion, that are physiologically compatible, especially when used in humans and/or mammals. In the context of the present invention the term is particularly understood to denote the salt formed with a physiologically compatible acid, namely salts of the respective active constituent with inorganic or organic acids, that are physiologically compatible, especially when used in humans and/or mammals. Examples of physiologically compatible salts of specific acids include salts of hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro1$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid and/or aspartic acid. The hydrochloride salt is particularly preferred.

In one preferred embodiment of a compound according to the invention, R is selected from phenyl, benzyl or phenyl condensed with a heteroaryl, each mono- or polysubstituted or unsubstituted, respectively. Preferably R is selected from phenyl, benzyl or phenyl condensed with a heteroaryl, each unsubstituted or mono- or disubstituted with OH, F, Cl, Br, I, —CF$_3$, —OCH$_3$, —OC$_2$H$_5$, —CH$_3$, and/or —C$_2$H$_5$. Especially preferably, R is selected from 4-nitrophenyl, benzo[1,2,5]oxadiazole or unsubstituted phenyl.

In another preferred embodiment of a compound according to the invention, R' is selected from n-butyl or butan-4-ol; cyclopentyl, tetrahydrofuranyl or tetrahydropyranyl, unsubstituted respectively; benzyl, unsubstituted or mono- or disubstituted with NO$_2$, F, phenyl, I, Cl, trifluoromethoxy, trifluoromethyl or methoxy; or -butyl-O-tetrahydropyranyl. Preferably R' denotes benzyl.

In yet another preferred embodiment of a compound according to the invention, R" is selected from NH—C$_{1-6}$-alkyl, NH—C$_{3-8}$-cycloalkyl, N(C$_{1-6}$-alkyl)$_2$, piperidine, morpholine or pyrrolidine, mono- or polysubstituted respectively, preferably NH—C$_{1-6}$-alkyl, NH—C$_{3-6}$-cycloalkyl, piperidine, morpholine or pyrrolidine.

In a preferred embodiment of a compound according to the invention, Y denotes H.

In still another preferred embodiment, the compound is selected from the group consisting of:
9-Benzyl-8-(cyclopentylamine)-6-(4-nitrobenzyl)-6-mercaptopurine;
9-Benzyl-8-(cyclohexylamine)-6-(4-nitrobenzyl)-6-mercaptopurine;
9-Benzyl-6-(4-nitrobenzyl)-8-pyrrolidino-6-mercaptopurine;
9-Benzyl-8-morpholino-6-(4-nitrobenzyl)-6-mercaptopurine;
6-(Benzo[1,2,5]oxadiazol-5-ylmethylsulfanyl)-9-benzyl-8-pyrrolidin-1-yl-9H-purine;
6-(Benzo[1,2,5]oxadiazol-5-ylmethylsulfanyl)-9-benzyl-8-morpholin-4-yl-9H-purine;
9-Benzyl-6-benzylsulfanyl-8-morpholin-4-yl-9H-purine, and
9-Benzyl-6-benzylsulfanyl-8-pyrrolidin-1-yl-9H-purine.

The nitrobenzylthioinosine derivatives according to the invention are surprisingly effective in the treatment of pain and in other indications. Therefore, a further object of the invention is a pharmaceutical composition comprising at least one derivative of nitrobenzylthioinosine according to the invention as active ingredient as well as optionally at least one auxiliary material and/or additive. The auxiliary material and/or additive can be a carrier, excipient, support material, glidant, filler, solvent, diluent, colorant, taste conditioner such as a sugar, antioxidant and/or binder. In the case of a suppository this might involve waxes or fatty acid esters or conserving agents, emulsifiers and/or carriers for parenteral application. The selection of these auxiliary materials and/or additives and of the amounts to be used depends upon how the pharmaceutical composition is to be administered.

Example routes of administration include oral or parenteral such as pulmonal, nasal, rectal and/or intravenous administration. Therefore the pharmaceutical composition according to the invention can be adapted for topical or systemical application, especially dermal, subcutaneous, intramuscular, intra-articular and/or intraperitoneal, pulmonal, buccal, sublingual, nasal, percutaneous, vaginal, oral or parenteral, pulmonal, nasal, rectal and/or intravenous administration. For example, for use in treatment the pharmaceutical composition according to the invention might preferably be in the form of a plaster and/or gauze providing an occlusion of the burned or wounded skin. Preparations in the form of tablets, chewable tablets, dragees, capsules, granules, drops, juices and syrups are suitable for oral administration. Solutions, suspensions, readily reconstitutable dry preparations and sprays are suitable i.a. for parenteral application. Examples of suitable percutaneous forms of application include the compounds according to the invention as a depot in dissolved form or in a patch, optionally with the addition of agents which promote dermal penetration. Topical administration forms include, inter alia, ointments, gels, creams, lotions, suspensions and emulsions, whereas the preferred form for rectal application is a suppository. Therefore, in a preferred object of the invention the pharmaceutical composition according to the invention is in the form of an ointment, a gel, a cream, a lotion, a suspension, an emulsion, a suppository, a solution, a tablet, a chewable tablet, a dragee, a capsule, a granules, drops, a juice and/or a syrup.

The compounds according to the invention can be released in a delayed manner from forms of preparations which can be applied as mentioned above, especially orally, rectally or percutaneously. Retard formulations are preferred objects of the invention.

The amount of active ingredient to be administered to the patient varies depending on the weight of the patient, on the type of administration, the indication being treated, and on the severity of the illness. 1 to 500 mg of the active ingredient are usually applied per kg of patient body weight.

A further preferred aspect of the invention relates to pharmaceutical compositions containing at least 0.05 bis 90.0% of active ingredient.

As previously noted, the nitrobenzylthioinosine compounds according to the invention are surprisingly effective in the treatment of pain and in other indications. Therefore a further aspect of the invention relates to the use of a nitrobenzylthioinosine compound according to the invention for the treatment of pain, especially acute, chronic and/or neuropathic pain.

A still further aspect of the invention relates to the use of a nitrobenzylthioinosine compound according to the invention for the treatment of epilepsy and other CNS-related disorders, as well as for neuroprotection or cardioprotection. Furthermore the invention relates to a method of treatment using nitrobenzylthioinosine compounds according to the invention especially for the treatment of pain, especially acute, chronic and/or neuropathic pain; the treatment of epilepsy and other CNS-related disorders as well as for neuroprotection or cardioprotection.

EXAMPLES

The following examples are intended to illustrate the invention in further detail without limiting its scope.

Column chromatography was performed on Baker Silica Gel (0.063-0.200 mm). For TLC analysis, Schleicher and Schuell F1500/LS 254 silica plates were used. Spots were visualised with ultraviolet light. Microwave reactions were performed in an Emrys™ Optimizer. $^1$H NMR and $^{13}$C NMR were recorded with a Bruker AC 200 spectrometer at room temperature unless indicated otherwise. Tetramethylsilane was used as internal standard; δ in ppm, J in Hz. Melting points were determined with a Buchi melting point apparatus and are uncorrected. High Resolution Mass spectroscopy was performed on a PE-Sciex API Qstar instrument.

General Procedure A:

To a solution of 2',3',5'-tri-O-acetyl-8-bromoinosine in dioxane (10 mL per mmol) was added the appropriate alkylamine (14 eq). After stirring for 3 days at 80° C. the reaction mixture was evaporated to dryness. The residue was dissolved in dry pyridine and evaporated to dryness (two times). To a solution of the resulting residue in pyridine (3.5 mL per mmol) were added acetic acid anhydride (0.85 mL per mmol) and a catalytic amount of DMAP. The mixture was stirred for 4 hours before methanol was added (1.5 mL per mmol). After evaporation of the solvents the residue was dissolved in dichloromethane (20 mL per mmol), and the organic layer was washed with 10% NaHCO$_3$ (10 mL per mmol) and water (10 mL per mmol). The organic layer was dried (MgSO$_4$), filtered and concentrated to dryness. Remaining pyridine was Scheme 1:

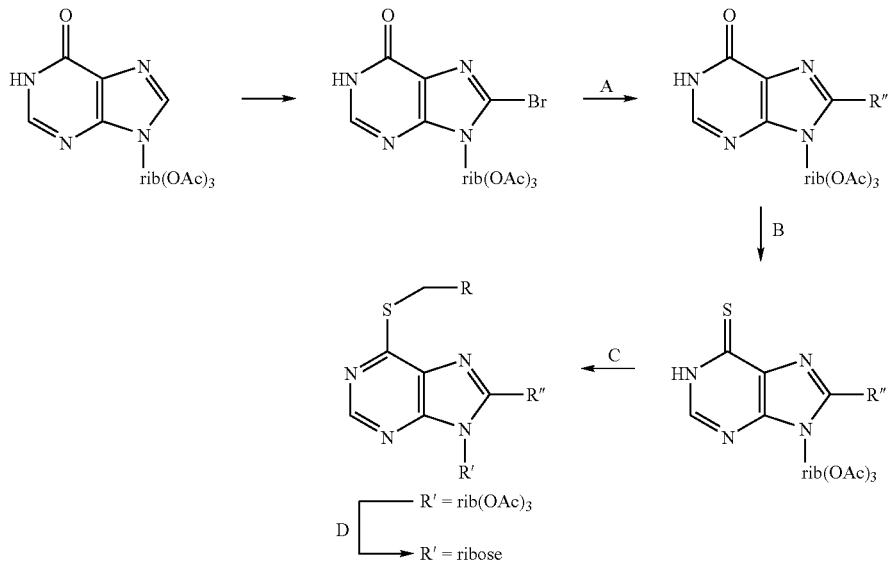

Scheme 2:

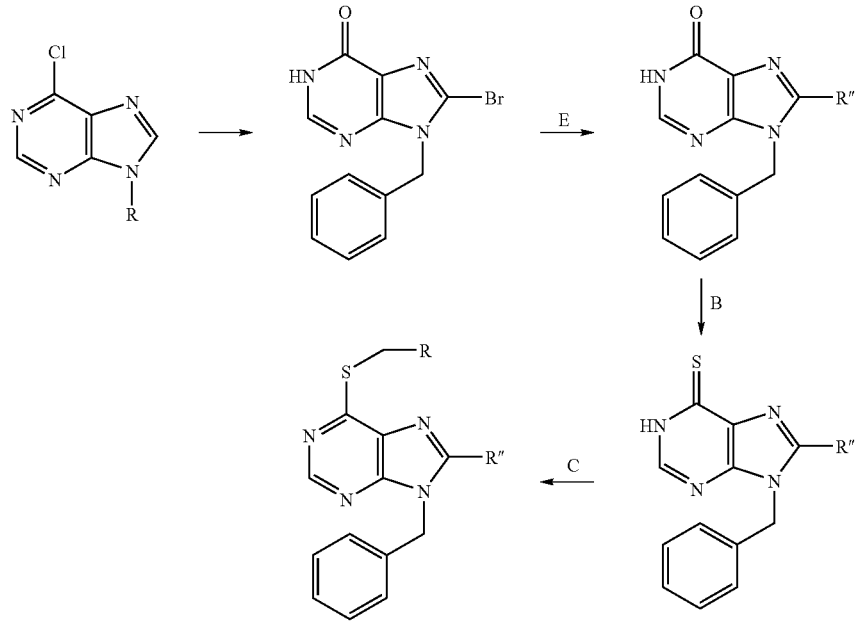

removed by coevaporation with toluene and dichloromethane. The product was purified by column chromatography (eluent: CH$_2$Cl$_2$/MeOH, 100/0→95/5, v/v).

General Procedure B:

Per mmol of purine derivative obtained in procedure A or E (3× coevaporated with dry pyridine) in 25 mL of dry pyridine was added 1.75 g of phosphorous pentasulfide and the resulting mixture was refluxed for 7 h. After evaporation of the solvent the residual solvent was removed by coevaporation with methanol (MeOH) (2×). Water was added and the resulting mixture was stirred for 1 h at 50° C. After extraction with ethyl acetate (EtOAc) (3×15 mL), the combined organic layers were dried over sodium sulfate (Na$_2$SO$_4$), filtrated, and the solvent was evaporated. The product was purified by column chromatography (eluent: EtOAc/MeOH, 97/3→95/5 v/v).

General Procedure C:

Per mmol of substituted purine derivative obtained in procedure B in 7.5 mL of dry dimethyl formamide (DMF) was added 1 eq. of K$_2$CO$_3$ and 1.2 eq. of RCH$_2$Br. After stirring overnight at r.t. 10 mL of water was added, the mixture extracted with EtOAc (3×10 mL), the combined organic layers washed with brine (15 mL), dried (Na$_2$SO$_4$), filtered, and the solvent was evaporated. The product was purified by column chromatography (eluent: EtOAc/PE 40-60, 1/1→6/4 v/v).

General Procedure D:

25 mL of MeOH, saturated with NH$_3$, were added at 0° C. to 1 mmol of the corresponding purine derivative obtained in procedure C. After stirring overnight the solvent was evaporated and the product purified by column chromatography (eluent: EtOAc/MeOH, 95/5→90/10 v/v). The appropriate fractions were collected and evaporated to dryness. Residual EtOAc was removed by dissolving the product in CH$_2$Cl$_2$ followed by evaporation (two times).

General Procedure E:

Per mmol of brominated purine derivative from Scheme 2 were added 6 mL of dioxane and 2.4 mL of water followed by 7.5 eq. of the required amine. The mixture was heated in an Emrys™ Optimizer microwave for 5 h at 175° C. or 2.5 h at 150° C. After removal of the solvents by evaporation dioxane was added and the mixture evaporated to dryness. The product was purified by column chromatography (eluent: CH$_2$Cl$_2$/MeOH, 99/1→90/10 v/v).

6-benzylthiolnosine This compound was prepared according to a literature procedure (Fleming, S. A.; Rawlins, D. B.; Samano, V.; Robins, M. J. *J. Org. Chem.* 1992, 57, 5968-5976).

2',3',5'-tri-O-acetyl-inosine This compound was prepared according to a literature procedure (Roelen, H.; Veldman, N.; Spek, A. L.; von Frijtag Drabbe Künzel, J.; Mathôt, R. A. A.; Ijzerman, A. P. *J. Med. Chem.* 1996, 39, 1463-1471).

2',3',5'-tri-O-acetyl-8-bromoinosine This compound was prepared according to a literature procedure (Roelen, H.; Veldman, N.; Spek, A. L.; von Frijtag Drabbe Künel, J.; Mathôt, R. A. A.; Ijzerman, A. P. *J. Med. Chem.* 1996, 39, 1463-1471).

2',3',5'-tri-O-acetyl-8-(methylamino)-inosine This compound was prepared according to general procedure A applying methylamine (40% in H$_2$O, 15 mL per mmol). Yield: 65%. White solid. $^1$H NMR (CDCl$_3$) δ 2.04, 2.15, 2.16 (3×s, 3×3H, 3×CH$_3$CO), 3.11 (d, 3H, J=4.9 CH$_3$N), 4.26-4.41 (m, 2H, H-4', 1×H-5'), 4.54-4.68 (m, 1H, 1×H-5'), 5.09 (q, 1H, J=4.9, CH$_3$NH), 5.46 (dd, 1H, J=3.8, J=6.2, H-3'), 5.71 (t, 1H, J=6.6, H-2'), 6.18 (d, 1H, J=6.8, H-1'), 7.97 (s, 1H, H-2), 11.55 (br s, 1H, NH). $^{13}$C NMR (CDCl$_3$) δ 19.9, 20.1, 20.3, 29.5, 62.6, 69.6, 70.4, 79.9, 84.4, 121.9, 142.5, 148.0, 151.8, 157.6, 169.1, 169.3, 169.8.

2',3',5'-tri-O-acetyl-8-(ethylamino)-inosine This compound was prepared according to a literature procedure (Roelen, H.; Veldman, N.; Spek, A. L.; von Frijtag Drabbe Künel, J.; Mathôt, R. A. A.; Ijzerman, A. P. *J. Med. Chem.* 1996, 39, 1463-1471).

2',3',5'-tri-O-acetyl-8-(n-propylamino)-inosine This compound was prepared according to general procedure A applying n-propylamine (11.5 mL per mmol) and H$_2$O (5 mL per mmol). Yield: 58%. Yellowish foam. $^1$H NMR (CDCl$_3$) δ 0.96 (t, 3H, J=7.3, CH$_3$CH$_2$), 1.70 (sextet, 2H, J=7.3, CH$_3$CH$_2$), 2.05, 2.13, 2.15 (3×s, 3×3H, 3×CH$_3$CO), 3.35-3.67 (m, 2H, CH$_2$N), 4.27-4.42 (m, 2H, H-4', 1×H-5'), 4.51-4.63 (m, 1H, 1×H-5'), 5.06 (t, 1H, J=5.9, CH$_2$NH), 5.48 (dd, 1H, J=4.0, J=5.8, H-3'), 5.79 (t, 1H, J=6.2, H-2'), 6.12 (d, 1H, J=6.6, H-1'), 7.92 (s, 1H, H-2), 11.55 (br s, 1H, NH). $^{13}$C NMR (CDCl$_3$) δ 10.9, 19.8, 20.1, 20.2, 22.2, 44.5, 62.6, 69.5, 70.5, 79.8, 84.5, 121.9, 142.1, 147.9, 151.1, 157.6, 169.1, 169.2, 169.8.

2',3',5'-tri-O-acetyl-8-(n-butylamino)-inosine This compound was prepared according to general procedure A applying n-butylamine. Yield: 47%. Yellowish foam. $^1$H NMR (CDCl$_3$) δ 0.96 (t, 3H, J=7.3, CH$_3$CH$_2$), 1.29-1.69 (m, 2H, CH$_3$CH$_2$), 1.57-1.75 (m, 2H, CH$_2$CH$_2$N), 2.05, 2.12, 2.15 (3×s, 3×3H, 3×CH$_3$CO), 3.37-3.68 (m, 2H, CH$_2$N), 4.27-4.41 (m, 2H, H-4', 1×H-5'), 4.48-4.63 (m, 1H, 1×H-5'), 5.00 (t, 1H, J=5.9, CH$_2$NH), 5.49 (dd, 1H, J=4.4, J=5.9, H-3'), 5.79 (t, 1H, J=6.2, H-2'), 6.11 (d, 1H, J=6.6, H-1'), 7.91 (s, 1H, H-2), 11.40 (br s, 1H, NH). $^{13}$C NMR (CDCl$_3$) δ 13.4, 19.7, 19.9, 20.1, 20.3, 31.2, 42.6, 62.7, 69.6, 70.5, 79.9, 84.6, 122.0, 142.2, 148.0, 151.2, 157.7, 169.1, 169.3, 169.8.

2',3',5'-tri-O-acetyl-8-(n-pentylamino)-inosine This compound was prepared according to general procedure A applying n-pentylamine. Yield: 81%. Yellow foam. $^1$H NMR (CDCl$_3$) δ 0.90 (t, 3H, J=6.6, CH$_3$CH$_2$), 1.21-1.47 (m, 4H, 2×CH$_2$), 1.56-1.79 (m, 2H, CH$_2$CH$_2$N), 2.05, 2.12, 2.15 (3×s, 3×3H, 3×CH$_3$CO), 3.35-3.68 (m, 2H, CH$_2$N), 4.87-4.41 (m, 2H, H-4', 1×H-5'), 4.49-4.63 (m, 1H, 1×H-5'), 5.03 (t, 1H, J=5.9, CH$_2$NH), 5.49 (dd, 1H, J=4.4, J=6.2, H-3'), 5.80 (t, 1H, J=6.2, H-2'), 6.12 (d, 1H, J=6.2, H-1'), 7.97 (s, 1H, H-2), 11.24 (br s, 1H, NH). $^{13}$C NMR (CDCl$_3$) δ 13.5, 19.8, 20.0, 20.1, 21.9, 28.5, 28.7, 42.7, 62.6, 69.5, 70.5, 79.7, 84.5, 121.9, 142.0, 147.8, 151.1, 157.5, 169.0, 169.1, 169.7.

2',3',5'-tri-O-acetyl-8-(n-hexylamino)-inosine This compound was prepared according to general procedure A applying n-hexylamine. Yield: 43%. Yellowish oil. $^1$H NMR (CDCl$_3$) δ 0.89 (t, 3H, J=6.6, CH$_3$CH$_2$), 1.21-1.48 (m, 6H, 3×CH$_2$), 1.60-1.74 (m, 2H, CH$_2$CH$_2$N), 2.05, 2.12, 2.15 (3×s, 3×3H, 3×CH$_3$CO), 3.37-3.67 (m, 2H, CH$_2$N), 4.27-4.43 (m, 2H, H-4', 1×H-5'), 4.49-4.63 (m, 1H, 1×H-5'), 5.03 (t, 1H, J=5.8, CH$_2$NH), 5.51 (dd, 1H, J=4.2, J=6.0, H-3'), 5.80 (t, 1H, J=6.2, H-2'), 6.13 (d, 1H, J=6.2, H-1'), 7.98 (s, 1H, H-2), 11.12 (br s, 1H, NH). $^{13}$C NMR (CDCl$_3$) δ 13.4, 19.7, 19.9, 20.0, 26.0, 28.8, 30.9, 42.7, 62.5, 69.4, 70.5, 79.6, 84.5, 121.9, 142.0, 147.7, 151.0, 157.4, 168.9, 169.1, 169.6.

2',3',5'-tri-O-acetyl-8-[(2-methyl-butyl)-amino]-inosine This compound was prepared according to general procedure A applying 2-methyl-butylamine. Yield: 27%. Colorless oil. $^1$H NMR (CDCl$_3$) δ 0.87-0.99 (m, 6H, 2×CH$_3$), 1.05-1.28 (m, 1H, CH$_3$CHH), 1.39-1.62 (m, 1H, CH$_3$CHH), 1.69-1.90 (m, 1H, CH$_3$CH), 2.06, 2.11, 2.15 (3×s, 3×3H, 3×CH$_3$CO), 3.17-3.34 (m, 0.5H, CHHNH), 3.36-3.46 (m, 1H, CHHNH), 3.47-3.66 (m, 0.5H, CHHNH), 4.24-4.61 (m, 3H, H-4', H-5'), 5.07 (t, 1H, J=5.9, NH), 5.46-5.55 (m, 1H, H-3'), 5.79-5.88 (m, 1H, H-2'), 6.07-6.15 (m, 1H, H-1'), 7.99 (s, 1H, H-2). $^{13}$C NMR (CDCl$_3$) δ 10.9, 16.7, 20.1, 20.2, 20.4, 26.6, 26.8, 34.1, 48.7, 62.8, 69.9, 70.7, 80.0, 84.7, 122.1, 142.1, 148.0, 151.4, 157.9, 169.2, 169.4, 169.9.

2',3',5'-tri-O-acetyl-8-(cyclopropylamino)-inosine This compound was prepared according to general procedure A applying cyclopropylamine (1.7 mL per mmol) and H$_2$O (3.5 mL per mmol). Yield: 57%. Yellowish solid. $^1$H NMR (CDCl$_3$) δ 0.51-0.68 (m, 2H, CH$_2$CHN), 0.80-0.98 (m, 2H, CH$_2$CHN), 2.05, 2.14, 2.15 (3×s, 3×3H, 3'CH$_3$CO), 2.88-3.05 (m, 1H, CHN), 4.29-4.40 (m, 2H, H-4', 1×H-5'), 4.50 (ABX, 1H, J=4.8, J=12.8, 1×H-5'), 5.41 (br s, 1H, CH$_2$CHNH), 5.50 (dd, 1H, J=4.8, J=5.9, H-3'), 5.75 (t, 1H, J=6.2, H-2'), 6.10 (d, 1H, J=6.2, H-1'), 8.05 (s, 1H, H-2), 11.21 (br s, 1H, NH). $^{13}$C NMR (CDCl$_3$) δ 7.1, 20.0, 20.2, 20.4, 24.8, 62.6, 69.5, 70.9, 79.7, 84.9, 122.0, 143.1, 148.1, 154.5, 157.7, 169.2, 169.3, 170.0.

2',3',5'-tri-O-acetyl-8-(cyclopentylamino)-inosine This compound was prepared according to a literature procedure (Roelen, H.; Veldman, N.; Spek, A. L.; von Frijtag Drabbe Künel, J.; Mathôt, R. A. A.; Ijzerman, A. P. *J. Med. Chem.* 1996, 39, 1463-1471).

2',3',5'-tri-O-acetyl-8-(cyclohexylamino)-inosine This compound was prepared according to general procedure A applying cyclohexylamine. Yield: 28%. Colorless oil. $^1$H NMR (CDCl$_3$) δ 1.07-1.84 (m, 8H, 2×NHCHCHH, 3×CH$_2$), 2.06, 2.09, 2.14 (3×s, 3×3H, 3×CH$_3$CO), 2.07-2.25 (m, 2H, 2×NHCHCHH), 3.87-4.08 (m, 1H, CH$_2$CHNH), 4.29-4.41 (m, 3H, H-4', H-5'), 4.50 (ABX, 1H, J=4.7, J=12.8, 1×H-5'), 4.73 (d, 1H, J=7.5, CH$_2$CHNH), 5.53 (dd, 1H, J=4.6, J=5.9, H-3'), 5.88 (t, 1H, J=5.9, H-2'), 6.03 (d, 1H, J=5.9, H-1'), 7.91 (s, 1H, H-2), 11.31 (br s, 1H, NH). $^{13}$C NMR (CDCl$_3$) δ 20.1, 20.2, 20.5, 24.7, 25.4, 33.0, 33.2, 51.3, 62.7, 69.7, 71.0, 79.8, 84.9, 122.2, 141.9, 147.9, 150.6, 157.9, 169.3, 170.0.

2',3',5'-tri-O-acetyl-8-pyrrolidino-inosine This compound was prepared according to general procedure A applying pyrrolidine. Yield: 65%. White foam. $^1$H NMR (CDCl$_3$) δ 1.72-2.09 (m, 4H, 2×CH$_2$CH$_2$N), 2.06, 2.08, 2.12 (3×s, 3×3H, 3×CH$_3$CO), 3.52-3.75 (m, 4H, 2×CH$_2$N), 4.29-4.37 (m, 2H, H-4', 1×H-5'), 4.48 (ABX, 1H, J=6.0, J=13.7, 1×H-5'), 5.86 (dd, 1H, J=5.1, J=5.9, H-3'), 5.98 (d, 1H, J=4.9, H-1'), 6.40 (dd, 1H, J=4.9, J=5.9, H-2'), 7.97 (s, 1H, H-2), 11.44 (br s, 1H, NH). $^{13}$C NMR (CDCl$_3$) δ 19.8, 19.9, 20.0, 25.0, 50.7, 62.4, 69.9, 71.1, 79.0, 86.2, 122.5, 142.4, 147.8, 153.8, 157.4, 168.6, 168.8, 169.8.

2',3',5'-tri-O-acetyl-8-piperidino-inosine This compound was prepared according to general procedure A applying piperidine. Yield: 60%. White solid. $^1$H NMR (CDCl$_3$) δ 1.51-1.82 (m, 6H, (CH$_2$)$_3$CH$_2$N), 2.07, 2.09, 2.13 (3×s, 3×3H, 3×CH$_3$CO), 3.14-3.38 (m, 4H, 2×CH$_2$N), 4.28-4.38 (m, 2H, H-4', 1×H-5'), 4.51 (ABX, 1H, J=6.2, J=13.9, 1×H-5'), 5.84-5.96 (m, 2H, H-1', H-3'), 6.25 (dd, 1H, J=4.8, J=6.2, H-2'), 8.07 (s, 1H, H-2), 11.50 (br s, 1H, NH). $^{13}$C NMR (CDCl$_3$) δ 19.9, 20.1, 23.4, 24.9, 51.9, 62.5, 69.9, 71.5, 79.0, 86.2, 122.2, 143.8, 147.9, 155.2, 157.7, 168.6, 168.9, 169.9.

2',3',5'-tri-O-acetyl-8-N-morpholino-inosine This compound was prepared according to general procedure A applying morpholine. Yield: 40%. White solid. $^1$H NMR (CDCl$_3$) δ 2.06, 2.10, 2.14 (3×s, 3×3H, 3×CH$_3$CO), 3.21-3.49 (m, 4H, 2×CH$_2$N), 3.77-3.95 (m, 4H, 2×CH$_2$O), 4.26-4.55 (m, 3H, H-4', H-5'), 5.85-5.94 (m, 2H, H-1', H-3'), 6.29 (dd, 1H, J=4.6, J=6.0, H-2'), 8.10 (s, 1H, H-2), 11.52 (br s, 1H, NH). $^{13}$C NMR (CDCl$_3$) δ 19.9, 20.0, 51.0, 62.4, 65.7, 69.9, 71.4, 79.1, 86.1, 122.1, 144.1, 147.9, 153.9, 157.5, 168.7, 168.9, 169.9.

2',3',5'-tri-O-acetyl-8-methylamino-thioinosine This compound was prepared according to general procedure B. Yield: 63%. Yellow oil. $^1$H NMR (CDCl$_3$) δ 2.03, 2.14, 2.15 (3×s, 3×3H, 3×CH$_3$CO), 3.15-3.78 (d, 3H, J=4.8, CH$_3$N), 4.28-4.44 (m, 2H, H-4', 1×H-5'), 4.53-4.66 (m, 1H, 1×H-5'), 5.45 (dd, 1H, J=4.0, J=6.2, H-3'), 5.59 (q, 1H, J=4.8, NH), 5.66-5.76 (m, 1H, H-2'), 6.17 (d, 1H, J=6.6, H-1'), 8.11 (s, 1H, H-2). $^{13}$C NMR (CDCl$_3$) δ 20.1, 20.2, 20.4, 29.6, 62.7, 69.6, 70.7, 79.9, 84.9, 134.3, 142.6, 143.9, 153.7, 168.5, 169.4, 169.5, 170.1. MS (ESI) m/z Found: 440.1 [M+H]$^+$, Calcd: 440.1.

2',3',5'-tri-O-acetyl-8-ethylamino-thioinosine This compound was prepared according to general procedure B. Yield: 67%. Yellow solid. $^1$H NMR (CDCl$_3$) δ 1.34 (t, 3H, J=7.3, CH$_3$CH$_2$), 2.03, 2.13, 2.15 (3×s, 3×3H, 3×CH$_3$CO), 3.56-3.78 (m, 2H, CH$_2$N), 4.28-4.42 (m, 2H, H-4', 1×H-5'), 4.59 (dd, 1H, J=4.0, J=12.1, 1×H-5'), 5.29 (t, 1H, J=4.4, NH), 5.45 (dd, 1H, J=4.0, J=6.6, H-3'), 5.72 (t, 1H, J=6.6, H-2'), 6.12 (d, 1H, J=6.6, H-1'), 8.01 (s, 1H, H-2). $^{13}$C NMR (CDCl$_3$/CD$_3$OD 1/1, v/v) δ 13.7, 19.3, 19.4, 19.6, 37.1, 62.4, 69.9, 70.8, 79.2, 84.8, 134.7, 141.3, 143.4, 152.8, 168.8, 169.3, 169.5, 170.4. MS (ESI) m/z Found: 454.0 [M+H]$^+$, Calcd: 454.1.

2',3',5'-tri-O-acetyl-8-(n-propylamino)-thioinosine This compound was prepared according to general procedure B. Yield: 60%. Brown oil. $^1$H NMR (CDCl$_3$) δ 0.97 (t, 3H, J=7.3, CH$_3$CH$_2$), 1.59-1.81 (m, 2H, CH$_3$CH$_2$), 2.03, 2.12, 2.15 (3×s, 3×3H, 3×CH$_3$CO), 3.42-3.75 (m, 2H, CH$_2$N), 4.26-4.45 (m, 2H, H-4', 1×H-5'), 4.58 (dd, 1H, J=4.0, J=12.1, 1×H-5'), 5.36 (t, 1H, J=5.5, NH), 5.46 (dd, 1H, J=4.4, J=6.6, H-3'), 5.76 (t, 1H, J=6.6, H-2'), 6.14 (d, 1H, J=6.6, H-1'), 8.05 (s, 1H, H-2), 11.67 (br s, 1H, NH). $^{13}$C NMR (CDCl$_3$) δ 10.8, 19.8, 20.1, 20.5, 22.1, 44.5, 62.5, 69.5, 70.5, 79.9, 84.6, 134.4, 142.0, 143.8, 152.8, 168.8, 169.0, 169.2, 169.8.

2',3',5'-tr-O-acetyl-8-(n-butylamino)-thioinosine This compound was prepared according to general procedure B. Yield: 61%. Yellow oil. $^1$H NMR (CDCl$_3$) δ 0.94 (t, 3H, J=7.3, CH$_3$CH$_2$), 1.30-1.50 (m, 2H, CH$_3$CH$_2$), 1.57-1.75 (m, 2H, CH$_2$CH$_2$NH), 2.04, 2.12, 2.15 (3×s, 3×3H, 3×CH$_3$CO), 3.46-3.77 (m, 2H, CH$_2$N), 4.26-4.44 (m, 2H, H-4', 1×H-5'), 4.58 (dd, 1H, J=4.0, J=12.1, 1×H-5'), 5.30 (t, 1H, J=5.5, NH), 5.45 (dd, 1H, J=4.0, J=6.2, H-3'), 5.76 (dd, 1H, J=6.2, J=6.6, H-2'), 6.13 (d, 1H, J=6.6, H-1'), 8.04 (s, 1H, H-2), 11.63 (br s, 1H, NH). $^{13}$C NMR (CDCl$_3$) δ 13.5, 19.7, 20.0, 20.2, 20.4, 31.2, 42.8, 62.7, 69.6, 70.6, 80.2, 84.6, 134.5, 142.1, 144.0, 152.9, 168.8, 169.2, 169.4, 169.9.

2',3',5'-tri-O-acetyl-8-(n-pentylamino)-thioinosine This compound was prepared according to general procedure B. Yield: 45%. Yellow-brown foam. $^1$H NMR (CDCl$_3$) δ 0.89 (t, 3H, J=6.6, CH$_3$CH$_2$), 1.23-1.43 (m, 4H, 2×CH$_2$), 1.56-1.75 (m, 2H, CH$_2$CH$_2$NH), 2.03, 2.12, 2.15 (3×s, 3×3H, 3×CH$_3$CO), 3.42-3.76 (m, 2H, CH$_2$N), 4.22-4.44 (m, 2H, H-4', 1×H-5'), 4.57 (ABX, 1H, J=4.4, J=11.7, 1×H-5'), 5.34 (t, 1H, J=5.1, CH$_2$NH), 5.46 (dd, 1H, J=3.7, J=5.9, H-3'), 5.74 (dd, 1H, J=5.9, J=6.6, H-2'), 6.13 (d, 1H, J=6.6, H-1'), 8.07 (s, 1H, H-2), 11.47 (br s, 1H, NH). $^{13}$C NMR (CDCl$_3$) δ 13.4, 19.8, 20.1, 20.2, 21.8, 28.6, 28.8, 42.8, 62.5, 69.4, 70.5, 79.9, 84.5, 134.4, 142.0, 143.8, 152.7, 168.5, 169.1, 169.2, 169.8.

2',3',5'-tri-O-acetyl-8-(n-hexylamino)-thioinosine This compound was prepared according to general procedure B. Yield: 58%. Yellow oil. $^1$H NMR (CDCl$_3$) δ 0.89 (t, 3H, J=6.6, 1×CH$_3$CH$_2$), 1.25-1.44 (m, 6H, 3×CH$_2$), 1.55-1.77 (m, 2H, CH$_2$CH$_2$NH), 2.04, 2.12, 2.15 (3×s, 3×3H, 3×CH$_3$CO), 3.44-3.77 (m, 2H, CH$_2$N), 4.26-4.44 (m, 2H, H-4', 1×H-5'), 4.58 (dd, 1H, J=4.4, J=11.7, 1×H-5'), 5.29 (t, 1H, J=5.1, NH), 5.45 (dd, 1H, J=4.4, J=6.6, H-3'), 5.73 (t, 1H, J=6.6, H-2'), 6.13 (d, 1H, J=6.6, H-1'), 8.02 (s, 1H, H-2), 11.68 (br s, 1H, NH). $^{13}$C NMR (CDCl$_3$) δ 13.7, 20.1, 20.3, 20.4, 22.2, 26.2, 29.2, 31.2, 43.1, 62.7, 69.6, 70.6, 80.3, 84.7, 134.5, 142.0, 144.1, 152.9, 168.8, 169.2, 169.4, 169.9.

2',3',5'-tri-O-acetyl-8-[(2-methyl-butyl)-amino]-thioinosine This compound was prepared according to general procedure B. Yield: 44%. Yellow oil. $^1$H NMR (CDCl$_3$) δ 0.87-1.00 (m, 6H, 2×CH$_3$), 1.07-1.31 (m, 1H, CH$_3$CHH), 1.37-1.60 (m, 1H, CH$_3$CHH), 1.64-1.92 (m, 1H, CH$_3$CH), 2.04, 2.10, 2.15 (3×s, 3×3H, 3×CH$_3$CO), 3.27-3.70 (m, 2H, CH$_2$N), 4.26-4.45 (m, 2H, H-4', 1×H-5'), 4.55 (dd, 1H, J=3.7, J=12.1, 1×H-5'), 5.30 (t, 1H, J=5.5, NH), 5.46 (dd, 1H, J=4.4, J=6.2, H-3'), 5.77 (t, 1H, J=6.2, H-2'), 6.11 (d, 1H, J=6.2, H-1'), 8.01 (s, 1H, H-2), 11.76 (br s, 1H, NH). $^{13}$C NMR (CDCl$_3$) δ 10.9, 16.8, 20.1, 20.3, 20.5, 26.6, 26.8, 34.2, 48.8, 62.8, 69.7, 70.7, 80.3, 84.8, 134.6, 142.0, 144.2, 153.1, 168.8, 169.3, 169.5, 170.0.

2',3',5'-tri-O-acetyl-8-(cyclopropylamino)-thioinosine This compound was prepared according to general procedure B. Yield: 49%. Yellow oil. $^1$H NMR (CDCl$_3$) δ 0.58-0.70 (m, 2H, 2×CHH), 0.81-0.94 (m, 2H, CH$_2$CH$_2$NH), 2.05, 2.14; 2.16 (3×s, 3×3H, 3×CH$_3$CO), 2.98-3.13 (m, 1H, CHN), 4.26-4.41 (m, 2H, H-4', 1×H-5'), 4.46-4.60 (m, 1H, 1×H-5'), 5.46 (dd, 1H, J=4.4, J=5.9, H-3'), 5.65-5.77 (m, 2H, H-2', CHNH), 6.13 (d, 1H, J=5.8, H-1'), 8.17 (s, 1H, H-2), 11.75 (br s, 1H, NH). $^{13}$C NMR (CDCl$_3$) δ 7.3, 20.1, 20.3, 20.5, 24.8, 62.6, 69.6, 70.8, 80.0, 84.9, 134.2, 143.1, 143.9, 153.4, 169.3, 169.5, 169.6, 170.1.

2',3',5'-tri-O-acetyl-8-(cyclopentylamino)-thioinosine This compound was prepared according to general procedure B. Yield: 22%. Brownish oil. $^1$H NMR (CDCl$_3$) δ 1.41-1.70 (m, 8H, 4×CH$_2$), 2.05, 2.06, 2.15 (3×s, 3×3H, 3×CH$_3$CO), 4.29-4.63 (m, 4H, H-4', H-5', CHNH), 5.15 (d, 1H J=5.6, CHNH), 5.49 (t, 1H, J=5.9, H-3'), 5.81 (t, 1H, J=5.9, H-2'), 6.04 (d, 1H, J=5.9, H-1'), 8.01 (s, 1H, H-2), 11.77 (br s, 1H, NH). $^{13}$C NMR (CDCl$_3$) δ 20.1, 20.3, 20.4, 23.3, 32.8, 32.9, 54.5, 62.7, 69.6, 71.0, 80.1, 85.0, 134.6, 142.0, 144.0, 152.7, 168.9, 169.4, 170.1.

2',3',5'-tri-O-acetyl-8-(cyclohexylamino)-thioinosine This compound was prepared according to general procedure B. Yield: 41%. Yellow solid. $^1$H NMR (CDCl$_3$) δ 1.05-1.85 (m, 8H, 2×NHCHCHH, 3×CH$_2$), 2.05, 2.11, 2.15 (3×s, 3×3H, 3×CH$_3$CO), 1.98-2.24 (m, 2H, 2×NHCHCHH), 4.02-4.23 (m, 1H, CH$_2$CHNH), 4.28-4.58 (m, 3H, H-4', H-5'), 5.07 (d, 1H, J=8.0, CH$_2$CHNH), 5.48 (dd, 1H, J=4.4, J=5.9, H-3'), 5.81 (dd, 1H, J=5.9, J=6.6, H-2'), 6.05 (d, 1H, J=6.6, H-1'), 7.99 (s, 1H, H-2), 11.79 (br s, 1H, NH). $^{13}$C NMR (CDCl$_3$) δ 20.1, 20.3, 20.6, 24.6, 25.3, 33.0, 33.3, 51.3, 62.7, 69.6, 70.9, 80.2, 84.9, 134.7, 141.9, 144.0, 152.3, 168.7, 169.3, 169.4, 170.1.

2',3',5'-tri-O-acetyl-8-pyrrolidino-thioinosine This compound was prepared according to general procedure B. Yield: 55%. Brownish oil. $^1$H NMR (CDCl$_3$) δ 1.78-2.09 (m, 4H, 2×CH$_2$CH$_2$), 2.03, 2.05, 2.11 (3×s, 3×3H, 3×CH$_3$CO), 3.60-3.82 (m, 4H, 2×CH$_2$N), 4.21-4.53 (m, 3H, H-4', H-5'), 5.80 (t, 1H, J=5.1, H-3'), 5.98 (d, 1H, J=5.1, H-1'), 6.40 (t, 1H, J=5.1, H-2'), 8.05 (s, 1H, H-2), 11.74 (br s, 1H, NH). $^{13}$C NMR (CDCl$_3$) δ 20.0, 20.1, 20.2, 25.3, 50.7, 62.5, 70.0, 70.9, 79.3, 86.3, 134.8, 141.9, 143.6, 155.3, 168.8, 169.0, 170.1, 170.7.

2',3',5'-tri-O-acetyl-8-piperidino-thioinosine This compound was prepared according to general procedure B. Yield: 82%. Brown oil. $^1$H NMR (CDCl$_3$) δ 1.56-1.83 (m, 6H, (CH$_2$)$_3$CH$_2$N), 2.05, 2.08, 2.14 (3×s, 3×3H, 3×CH$_3$CO), 3.22-3.49 (m, 4H, 2×CH$_2$N), 4.26-4.55 (m, 3H, H-4', H-5'), 5.79-5.88 (m, 2H, H-1', H-3'), 6.25 (t, 1H, J=5.5, H-2'), 8.10 (s, 1H, H-2), 12.05 (br s, 1H, NH). $^{13}$C NMR (CDCl$_3$) δ 19.9, 20.0, 20.2, 23.3, 24.9, 51.5, 62.4, 69.9, 71.1, 79.2, 86.4, 134.0, 143.3, 143.5, 157.0, 168.7, 169.0, 170.1, 170.6.

2',3',5'-tri-O-acetyl-8-N-morpholino-thioinosine This compound was prepared according to general procedure B.

Yield: 84%. Yellow oil. $^1$H NMR (CDCl$_3$) δ 2.07, 2.09, 2.15 (3×s, 3×3H, 3×CH$_3$CO), 3.27-3.42 (m, 2H, 2×CHHN), 3.44-3.59 (m, 2H, 2×CHHN), 3.78-3.99 (m, 4H, 2×CH$_2$N), 4.25-4.51 (m, 3H, H-4', H-5'), 5.81-5.90 (m, 2H, H-1', H-3'), 6.30 (dd, 1H, J=4.8, J=5.9, H-2'), 8.10 (s, 1H, H-2), 12.15 (br s, 1H, NH). $^{13}$C NMR (CDCl$_3$) δ 20.1, 20.2, 20.5, 50.7, 62.5, 65.8, 69.9, 71.1, 79.3, 86.3, 133.9, 143.4, 144.5, 155.9, 168.8, 169.1, 170.1, 170.7.

2',3',5'-tri-O-acetyl-6-benzyl-8-methylamino-thioinosine This compound was prepared according to general procedure C. Yield: 61%. White solid. $^1$H NMR (CDCl$_3$) δ 2.01, 2.13, 2.15 (3×s, 3×3H, 3×CH$_3$CO), 3.13 (d, 2H, J=5.1, CH$_3$N), 4.61 (m, 2H, H-4', 1×H-5'), 4.61 (ABX, 1H, J=3.7, J=11.7, 1×H-5'), 4.62 (s, 2H, CH$_2$S), 5.36 (t, 1H, J=5.1, NH), 5.47 (dd, 1H, J=3.4, J=6.2, H-3'), 5.73 (dd, 1H, J=6.2, J=6.9, H-2'), 6.24 (d, 1H, J=6.9, H-1'), 7.21-7.34 (m, 3H, CH arom), 7.43-7.49 (m, 2H, CH arom), 8.52 (s, 1H, H-2). $^{13}$C NMR (CDCl$_3$) δ 18.8, 18.9, 19.0, 31.1, 34.8, 61.6, 68.9, 69.9, 78.3, 83.9, 125.7, 127.0, 127.7, 130.1, 137.0, 146.9, 148.3, 149.9, 153.1, 167.9, 168.1, 168.8.

2',3',5'-tri-O-acetyl-6-benzyl-8-ethylamino-thioinosine This compound was prepared according to general procedure C. Yield: 52%. White solid. $^1$H NMR (CDCl$_3$) δ 1.30 (t, 3H, J=7.3, CH$_3$CH$_2$), 2.03, 2.09, 2.15 (3×s, 3×3H, 3×CH$_3$CO), 3.46-3.69 (m, 2H, CH$_2$N), 4.24-4.58 (m, 3H, H-4', H-5'), 4.62 (s, 2H, CH$_2$S), 5.24 (t, 1H, J=5.5, NH), 5.51 (dd, 1H, J=3.7, J=5.9, H-3'), 5.84 (t, 1H, J=6.2, H-2'), 6.17 (d, 1H, J=6.6, H-1'), 7.22-7.36 (m, 3H, CH arom), 7.38-7.47 (m, 2H, CH arom), 8.50 (s, 1H, H-2). $^{13}$C NMR (CDCl$_3$) δ 14.8, 20.2, 20.4, 20.5, 32.7, 37.9, 62.9, 70.0, 70.6, 80.5, 84.5, 126.9, 128.3, 129.0, 130.6, 137.7, 148.6, 149.2, 152.5, 152.9, 169.4, 169.5, 170.1.

2',3',5'-tri-O-acetyl-6-benzyl-8-(n-propylamino)-thioinosine This compound was prepared according to general procedure C. Yield: 59%. Yellowish solid. $^1$H NMR (CDCl$_3$) δ 0.97 (t, 3H, J=7.3, CH$_3$CH$_2$), 2.03, 2.07, 2.15 (3×s, 3×3H, 3×CH$_3$CO), 3.36-3.66 (m, 2H, CH$_2$N), 4.25-4.42 (m, 1H, H-4', 1×H-5'), 4.56 (ABX, 1H, J=3.7, J=11.7, 1×H-5'), 4.62 (s, 2H, CH$_2$S), 5.30 (t, 1H, J=5.9, NH), 5.52 (dd, 1H, J=4.0, J=5.9, H-3'), 5.87 (t, 1H, J=6.2, H-2'), 6.16 (d, 1H, J=6.2, H-1'), 7.17-7.34 (m, 3H, CH arom), 7.38-7.49 (m, 2H, CH arom), 8.50 (s, 1H, H-2). $^{13}$C NMR (CDCl$_3$) δ 11.0, 19.9, 20.1, 20.2, 22.2, 32.5, 44.5, 62.7, 69.8, 70.6, 80.0, 84.4, 126.7, 128.0, 129.1, 130.5, 137.5, 148.3, 149.0, 152.0, 152.9, 169.1, 169.2, 169.8.

2',3',5'-tri-O-acetyl-6-benzyl-8-(n-butylamino)-thioinosine This compound was prepared according to general procedure C. Yield: 66%. Off-white solid. $^1$H NMR (CDCl$_3$) δ 0.95 (t, 3H, J=7.3, CH$_3$CH$_2$), 1.30-1.50 (m, 2H, CH$_2$CH$_3$), 1.55-1.75 (m, 2H, CH$_2$CH$_2$N), 2.03, 2.07, 2.15 (3×s, 3×3H, 3×CH$_3$CO), 3.39-3.69 (m, 2H, CH$_2$N), 4.27-4.43 (m, 2H, H-4', 1×H-5'), 4.56 (ABX, 1H, J=3.7, J=11.7, 1×H-5'), 4.62 (s, 2H, CH$_2$S), 5.25 (t, 1H, J=5.4, NH), 5.53 (dd, 1H, J=4.4, J=5.9, H-3'), 5.87 (t, 1H, J=5.9, H-2'), 6.15 (d, 1H, J=5.9, H-1'), 7.17-7.34 (m, 3H, CH arom), 7.41-7.49 (m, 2H, CH arom), 8.50 (s, 1H, H-2). $^{13}$C NMR (CDCl$_3$) δ 13.6, 19.8, 20.1, 20.4, 31.4, 32.7, 42.8, 62.9, 69.9, 70.8, 80.3, 84.6, 126.9, 128.2, 128.9, 130.6, 137.7, 148.5, 149.2, 152.3, 153.0, 169.4, 169.5, 170.0.

2',3',5'-tri-O-acetyl-6-benzyl-8-(n-pentylamino)-thioinosine This compound was prepared according to general procedure C. Yield: 95%. Yellow oil. $^1$H NMR (CDCl$_3$) δ 0.85-0.94 (m, 3H, CH$_3$CH$_2$), 1.23-1.45 (m, 4H, 2×CH$_2$), 1.60-1.73 (m, 2H, CH$_2$CH$_2$N), 2.05, 2.07, 2.14 (3×s, 3×3H, 3×CH$_3$CO), 3.38-3.67 (m, 2H, CH$_2$N), 4.27-4.41 (m, 2H, H-4', 1×H-5'), 4.58 (dd, 1H, J=4.4, J=11.7, 1×H-5'), 4.62 (s, 2H, CH$_2$S), 5.03 (t, 1H, J=5.1, CH$_2$NH), 5.53 (dd, 1H, J=3.7, J=5.9, H-3'), 5.87 (t, 1H, J=5.9, H-2'), 6.16 (d, 1H, J=5.9, H-1'), 7.18-7.33 (m, 3H, CH arom), 7.45 (dd, 2H, J=1.5, J=8.0, CH arom), 8.50 (s, 1H, H-2). $^{13}$C NMR (CDCl$_3$) δ 13.5, 19.8, 20.0, 20.1, 21.9, 28.5, 28.6, 32.4, 42.7, 62.6, 69.7, 70.6, 79.9, 84.4, 126.6, 127.9, 128.6, 130.5, 137.5, 148.1, 149.0, 151.8, 152.8, 169.0, 169.1, 169.7.

2',3',5'-tri-O-acetyl-6-benzyl-8-(n-hexylamino)-thioinosine This compound was prepared according to general procedure C. Yield: 86%. White solid. $^1$H NMR (CDCl$_3$) δ 0.88 (t, 3H, J=6.6, CH$_3$CH$_2$), 1.25-1.45 (m, 4H, CH$_2$CH$_3$), 1.53-1.77 (m, 4H, CH$_2$CH$_2$N), 2.03, 2.07, 2.15 (3×s, 3×3H, 3×CH$_3$CO), 3.37-3.69 (m, 2H, CH$_2$N), 4.27-4.42 (m, 2H, H-4', 1×H-5'), 4.56 (ABX, 2H, J=3.7, J=11.7, 1×H-5'), 4.62 (s, 2H, CH$_2$S), 5.25 (t, 1H, J=5.4, NH), 5.53 (dd, 1H, J=3.7, J=5.9, H-3'), 5.85 (t, 1H, J=5.9, H-2'), 6.15 (d, 1H, J=5.9, H-1'), 7.17-7.37 (m, 3H, CH arom), 7.45 (dd, 2H, J=1.5, J=8.0 CH arom), 8.50 (s, 1H, H-2). $^{13}$C NMR (CDCl$_3$) δ 13.9, 20.1, 20.3, 20.8, 22.3, 26.3, 29.2, 31.2, 32.7, 43.0, 62.9, 69.9, 70.8, 80.3, 84.6, 126.9, 128.2, 128.9, 130.6, 137.7, 148.5, 149.2, 152.3, 153.0, 169.3, 169.4, 170.0.

2',3',5'-tri-O-acetyl-6-benzyl-8-[(2-methyl-butyl)-amino]-thioinosine This compound was prepared according to general procedure C. Yield: 64%. Yellow oil. $^1$H NMR (CDCl$_3$) δ 0.87-0.99 (m, 6H, 2×CH$_3$), 1.07-1.31 (m, 1H, CH$_3$CHH), 1.36-1.58 (m, 1H, CH$_3$CHH), 1.64-1.86 (m, 1H, CH$_3$CH), 2.04, 2.05, 2.15 (3×s, 3×3H, 3×CH$_3$CO), 3.18-3.33 (m, 0.5H, CHHNH), 3.36-3.46 (m, 1H, CHHNH), 3.49-3.65 (m, 0.5H, CHHNH), 4.25-4.43 (m, 2H, H-4', 1×H-5'), 4.48-4.59 (m, 1H, 1×H-5'), 4.62 (s, 2H, CH$_2$S), 5.28 (m, 1H, NH), 5.49-5.58 (m, 1H, H-3'), 5.86-5.95 (m, 1H, H-2'), 6.12-6.18 (m, 1H, H-1'), 7.16-7.34 (m, 3H, CH arom), 7.41-7.49 (m, 2H, CH arom), 8.49 (s, 1H, H-2). $^{13}$C NMR (CDCl$_3$) δ 11.1, 17.0, 20.2, 20.5, 26.8, 26.9, 32.8, 34.5, 48.8, 63.0, 70.0, 71.0, 80.4, 84.7, 127.0, 128.3, 129.0, 130.7, 137.8, 148.6, 149.2, 152.5, 153.2, 169.4, 169.5, 170.0.

2',3',5'-tri-O-acetyl-6-benzyl-8-(cyclopropylamino)-thioinosine This compound was prepared according to general procedure C. Yield: 64%. White solid. $^1$H NMR (CDCl$_3$) δ 0.59-0.69 (m, 2H, CH$_2$), 0.82-0.93 (m, 2H, CH$_2$), 2.02, 2.12, 2.14 (3×s, 3×3H, 3×CH$_3$CO), 2.88-3.01 (m, 2H, CH$_2$N), 4.27-4.39 (m, 2H, H-4', 1×H-5'), 4.46-4.58 (m, 1H, 1×H-5'), 4.64 (s, 2H, CH$_2$S), 5.47-5.56 (m, 1H, H-3'), 5.57 (d, 1H, J=1.5, NH), 5.78 (t, 1H, J=6.2, H-2'), 6.14 (d, 1H, J=6.2, H-1'), 7.17-7.35 (m, 3H, CH arom), 7.41-7.50 (m, 2H, CH arom), 8.51 (s, 1H, H-2). $^{13}$C NMR (CDCl$_3$) δ 7.0, 7.2, 20.1, 20.3, 20.4, 24.8, 32.7, 62.7, 69.8, 70.9, 80.1, 84.6, 126.9, 128.2, 128.9, 130.5, 137.6, 148.7, 149.0, 153.0, 153.3, 169.3, 169.4, 170.0.

2',3',5'-tri-O-acetyl-6-benzyl-8-(cyclopentylamino)-thioinosine This compound was prepared according to general procedure C. Yield: 63%. Colorless oil. $^1$H NMR (CDCl$_3$) δ 1.41-1.80 (m, 6H, NHCHCHH, 2×CH$_2$), 2.03, 2.05, 2.15 (3×s, 3×3H, 3×CH$_3$CO), 2.08-2.12 (m, 2H, NHCHCHH), 4.27-4.56 (m, 4H, H-4', H-5', CHNH), 4.62 (s, 2H, CH$_2$S), 5.08 (d, J=6.8, 1H, NH), 5.57 (dd, 1H, J=4.8, J=5.7, H-3'), 5.97 (t, 1H, J=5.7, H-2'), 6.05 (d, 1H, J=5.7, H-1'), 7.21-7.34 (m, 3H, CH arom), 7.45 (dd, 2H, J=1.8, J=8.1, CH arom), 8.49 (s, 1H, H-2). $^{13}$C NMR (CDCl$_3$) δ 20.3, 20.4, 20.5, 23.5, 32.8, 33.0, 33.1, 54.6, 62.8, 70.0, 71.3, 80.2, 85.0, 126.9, 128.3, 129.0, 130.8, 137.7, 148.5, 149.0, 152.5, 152.7, 169.5, 169.6, 170.2.

2',3',5'-tri-O-acetyl-6-benzyl-8-(cyclohexylamino)-thioinosine This compound was prepared according to general procedure C. Yield: 59%. Colorless oil. $^1$H NMR (CDCl$_3$) δ 1.12-1.84 (m, 8H, 2×NHCHCHH, 3×CH$_2$), 2.04, 2.05, 2.15 (3×s, 3×3H, 3×CH$_3$CO), 2.01-2.12 (m, 2H, 2×NHCHCHH), 3.81-4.03 (m, 1H, CH$_2$CHNH), 4.29-4.57 (m, 3H, H-4', H-5'), 4.62 (s, 2H, CH$_2$S), 5.01 (d, J=7.7, 1H, NH), 5.57 (dd, 1H, J=4.8, J=5.5, H-3'), 5.97 (t, 1H, J=5.5, H-2'), 6.07 (d, 1H, J=5.5, H-1'), 7.18-7.33 (m, 3H, CH arom), 7.45 (dd, 2H, J=1.8, J=8.0, CH arom), 8.48 (s, 1H, H-2). $^{13}$C NMR (CDCl$_3$) δ 20.3, 20.4, 20.6, 24.7, 25.5, 32.7, 32.9, 33.2, 51.5, 62.9, 70.0, 71.3, 80.2, 85.0, 126.9, 128.3, 129.0, 130.8, 137.7, 148.4, 149.0, 152.3, 169.5, 170.1.

2',3',5'-tri-O-acetyl-6-benzyl-8-pyrrolidino-thioinosine This compound was prepared according to general procedure C. Yield: 42%. Colorless oil. $^1$H NMR (CDCl$_3$) δ 1.90-2.09 (m, 4H, 2×CH$_2$N), 2.05, 2.06, 2.13 (3×s, 3×3H, 3×CH$_3$CO), 3.62-3.78 (m, 4H, 2×CH$_2$N), 4.26-4.37 (m, 1H, H-4', 1×H-5'), 4.45-4.57 (m, 1H, 1×H-5'), 4.61 (s, 2H, CH$_2$S), 5.95-6.03 (m, 2H, H-1', H-3'), 6.59 (dd, 1H, J=4.8, J=5.8, H-2'), 7.20-7.33 (m, 3H, CH arom), 7.40-7.48 (m, 2H, CH arom), 8.51 (s, 1H, H-2). $^{13}$C NMR (CDCl$_3$) δ 20.3, 20.4, 20.5, 25.6, 32.6, 50.8, 62.8, 70.5, 71.3, 79.6, 86.8, 126.9, 128.2, 129.0, 131.0, 137.7, 148.7, 149.4, 152.9, 155.7, 169.1, 169.3, 170.4.

2',3',5'-tri-O-acetyl-6-benzyl-8-piperldino-thioinosine This compound was prepared according to general procedure C. Yield: 48%. Colorless oil. $^1$H NMR (CDCb$_3$) δ 1.57-1.84 (m, 6H, 3×CH$_2$), 2.06, 2.07, 2.13 (3×s, 3×3H, 3×CH$_3$CO), 3.19-3.45 (m, 4H, 2×CH$_2$N), 4.29-4.41 (m, 2H, H-4', 1×H-5'), 4.52 (ABX, 1H, J=6.2, J=13.9, 1×H-5'), 4.62 (s, 2H, CH$_2$S), 5.84 (d, 1H, J=4.8, H-1'), 6.00 (t, 1H, J=5.9, H-3'), 6.38 (dd, 1H, J=4.8, J=5.9, H-2'), 7.17-7.34 (m, 3H, CH arom), 7.44 (dd, 2H, J=1.8, J=8.0, CH arom), 8.58 (s, 1H, H-2). $^{13}$C NMR (CDCl$_3$) δ 20.3, 20.4, 20.5, 23.8, 25.2, 32.5, 51.8, 62.8, 70.4, 71.4, 79.5, 86.9, 126.9, 128.2, 128.9, 131.1, 137.5, 149.0, 149.9, 155.5, 157.4, 168.9, 169.2, 170.3.

2',3',5'-tri-O-acetyl-6-benzyl-8-morpholino-thioinosine This compound was prepared according to general procedure C. Yield: 66%. Colorless oil. $^1$H NMR (CDCl$_3$) δ 2.06, 2.07, 2.14 (3×s, 3×3H, 3×CH$_3$CO), 3.24-3.29 (m, 2H, 2×CHHN), 3.42-3.57 (m, 2H, 2×CHHN), 3.77-3.97 (m, 4H, 2×CH$_2$O), 4.27-4.39 (m, 2H, H-4', 1×H-5'), 4.43-5.56 (m, 1H, 1×H-5'), 4.62 (s, 2H, CH$_2$S), 5.86 (d, 1H, J=4.6, H-1'), 6.01 (t, 1H, J=5.7, H-3'), 6.44 (dd, 1H, J=4.6, J=5.7, H-2'), 7.17-7.34 (m, 3H, CH arom), 7.45 (dd, 2H, J=1.8, J=8.0, CH arom), 8.61 (s, 1H, H-2). $^{13}$C NMR (CDCl$_3$) δ 20.1, 20.3, 20.4, 32.5, 50.9, 62.6, 65.8, 70.3, 71.3, 79.6, 86.6, 126.9, 128.2, 128.8, 129.7, 137.3, 148.8, 150.1, 156.3, 168.9, 169.2, 170.2.

Example 1

6-benzyl-8-methylamino-thioinosine This compound was prepared according to general procedure D from 2',3',5'-tri-O-acetyl-6-benzyl-8-methylamino-thioinosine. Yield: 83%. White solid. M.p.: 193° C. (dec.). $^1$H NMR (MeOD) δ 3.02 (s, 3H, CH$_3$), 3.76-3.89 (m, 2H, H-5'), 4.15 (dd, 1H, J=1.8, J=4.0, H-4'), 4.27 (dd, 1H, J=1.8, J=5.5, H-3'), 4.61 (s, 2H, CH$_2$S), 4.70 (dd, 1H, J=5.5, J=7.7, H-2'), 6.61 (d, 1H, J=7.7, H-1'), 7.17-7.33 (m, 3H, CH arom), 7.42 (dd, 2H, J=2.2, J=8.0, CH arom), 8.39 (s, 1H, H-2). $^{13}$C NMR (CDCl$_3$/MeOD 1/2) δ 29.2, 33.6, 62.6, 72.3, 72.6, 87.1, 88.3, 127.8, 129.1, 129.7, 131.7, 138.7, 148.7, 150.5, 152.1, 155.4. HRMS (ESI) m/z Found: 404.1408 [M+H]$^+$, Calcd: 404.1392. (C$_{18}$H$_{21}$N$_5$O$_4$S.0.15 CH$_2$Cl$_2$) C,H,N,S.

Example 2

6-benzyl-8-ethylamino-thioinosine This compound was prepared according to general procedure D from 2',3',5'-tri-O-acetyl-6-benzyl-8-ethylamino-thioinosine. Yield: 96%. White solid. M.p.: 102-104° C. $^1$H NMR (CDCl$_3$/MeOD 1/1, v/v) δ 1.21 (t, 3H, J=7.3, CH$_3$CH$_2$), 3.34-3.56 (m, 2H, CH$_2$N), 3.77 (ABX, 1H, J=1.1, J=12.4, 1×H-5'), 3.92 (ABX, 1H, J=2.0, J=12.4, 1×H-5'), 4.18-4.24 (m, 1H, H-4'), 4.30 (dd, 1H, J=1.6, J=5.5, H-3'), 4.61 (s, 2H, CH$_2$S), 4.70 (dd, 1H, J=5.5, J=7.1, H-2'), 5.90 (d, 1H, J=7.1, H-1'), 7.18-7.34 (m, 3H, CH arom), 7.40-7.48 (m, 2H, CH arom), 8.39 (s, 1H, H-2). $^{13}$C NMR (CDCl$_3$/MeOD 1/1, v/v) δ 14.6, 33.5, 38.1, 62.4, 72.0, 72.3, 86.8, 87.9, 127.6, 128.9, 129.5, 131.7, 138.4, 148.3, 150.1, 151.9, 154.3. HRMS (ESI) m/z Found: 418.1510 [M+H]$^+$, Calcd: 418.1549. (C$_{19}$H$_{23}$N$_5$O$_4$S.0.05 CH$_2$Cl$_2$) C,H,N,S.

Example 3

6-benzyl-8-(n-propylamino)-thioinosine This compound was prepared according to general procedure D from 2',3',5'-tri-O-acetyl-6-benzyl-8-(n-propylamino)-thioinosine. Yield: 78%. White solid. M.p.: 108° C. $^1$H NMR (MeOD) δ 0.97 (t, 3H, J=7.3, CH$_3$CH$_2$), 1.56-1.77 (m, 2H, CH$_3$CH$_2$), 3.34-3.50 (m, 2H, CH$_2$N), 3.74-3.86 (m, 2H, H-5'), 4.10-4.17 (m, 1H, H-4'), 4.21-4.29 (m, 1H, H-3'), 4.61 (s, 2H, CH$_2$S), 4.69 (dd, 1H, J=5.5, J=7.7, H-2'), 6.13 (d, 1H, J=7.7, H-1'), 7.13-7.31 (m, 3H, CH arom), 7.36-7.45 (m, 2H, CH arom), 8.37 (s, 1H, H-2). $^{13}$C NMR (MeOD) δ 11.8, 23.4, 33.8, 45.4, 62.9, 72.6, 72.8, 87.5, 88.4, 128.1, 129.4, 130.0, 132.0, 139.4, 149.1, 151.1, 152.1, 155.1. HRMS (ESI) m/z Found: 432.1746 [M+H]$^+$, Calcd: 432.1705. (C$_{20}$H$_{25}$N$_5$O$_4$S) C,H,N,S.

Example 4

6-benzyl-8-(n-butylamino)-thioinosine This compound was prepared according to general procedure D from 2',3',5'-tri-O-acetyl-6-benzyl-8-(n-butylamino)-thioinosine. Yield: 87%. White solid. M.p.: 86° C. $^1$H NMR (MeOD) δ 0.95 (t, 3H, J=7.3, CH$_3$CH$_2$), 1.31-1.51 (m, 2H, CH$_3$CH$_2$), 1.55-1.73 (m, 2H, CH$_2$CH$_2$N), 3.34-3.58 (m, 2H, CH$_2$N), 3.77-3.83 (m, 2H, H-5'), 4.11-4.16 (m, 1H, H-4'), 4.26 (dd, 1H, J=1.8, J=5.5, H-3'), 4.61 (s, 2H, CH$_2$S), 4.68 (dd, 1H, J=5.5, J=7.7, H-2'), 6.14 (d, 1H, J=7.7, H-1'), 7.15-7.31 (m, 3H, CH arom), 7.37-7.46 (m, 2H, CH arom), 8.37 (s, 1H, H-2). $^{13}$C NMR (MeOD) δ 14.2, 21.1, 32.2, 33.8, 43.4, 62.9, 72.6, 72.7, 87.5, 88.3, 128.0, 129.4, 130.0, 132.0, 139.3, 149.0, 151.0, 152.0, 155.0. HRMS (ESI) m/z Found: 446.1818. [M+H]$^+$, Calcd: 446.1862. (C$_{21}$H$_{27}$N$_5$O$_4$S) C,H,N,S.

Example 5

6-benzyl-8-(n-pentylamino)-thioinosine This compound was prepared according to general procedure D from 2',3',5'-tri-O-acetyl-6-benzyl-8-(n-pentylamino)-thioinosine. Yield: 83%. White foam. M.p.: 80-82° C. $^1$H NMR (MeOD) δ 0.89 (t, 3H, J=6.9, CH$_3$CH$_2$), 1.28-1.43 (m, 4H, 2×CH$_2$), 1.61-1.76 (m, 2H, CH$_2$CH$_2$N), 3.32-3.60 (m, 2H, CH$_2$N), 3.74-3.87 (m, 2H, H-5'), 4.12-4.18 (m, 1H, H-4'), 5.51 (dd, 1H, J=1.8, J=5.5, H-3'), 4.60 (s, 2H, CH$_2$S), 4.69, (dd, 1H, J=5.5, J=7.3, H-2'), 6.14 (d, 1H, J=7.3, H-1'), 7.12-7.31 (m, 3H, CH arom), 7.40 (dd, 2H, J=1.5, J=8.0, CH arom), 8.36 (s, 1H, H-2). $^{13}$C NMR (MeOD) δ 14.4, 23.3, 29.7, 30.1, 33.8, 43.7, 62.8, 72.7, 87.4, 91.1, 128.0, 129.3, 129.9, 131.9, 139.1, 148.9, 150.8, 152.0, 154.9. HRMS (ESI) m/z Found: 460.2022. [M+H]$^+$, Calcd: 460.2018. Elem. anal. (C$_{22}$H$_{29}$N$_5$O$_4$S.0.1 CH$_2$Cl$_2$) C,H,N,S.

Example 6

6-benzyl-8-(n-hexylamino)-thioinosine This compound was prepared according to general procedure D from 2',3',5'-tri-O-acetyl-6-benzyl-8-(n-hexylamino)-thioinosine. Yield: 61%. Colorless glass. M.p.: 78° C. $^1$H NMR (MeOD) δ 0.88 (m, 3H, CH$_3$CH$_2$), 1.21-1.48 (m, 6H, 3×CH$_2$), 1.57-1.74 (m, 2H, CH$_2$CH$_2$N), 3.33-3.56 (m, 2H, CH$_2$N), 3.74-3.87 (m, 2H, H-5'), 4.14 (d, 1H, J=1.8, J=3.7, H-4'), 4.27 (dd, 1H, J=1.8, J=5.5, H-3'), 4.60 (s, 2H, CH$_2$S), 4.68 (dd, 1H, J=5.5, J=7.7, H-2'), 6.14 (d, 1H, J=7.7, H-1'), 7.13-7.30 (m, 3H, CH arom), 7.36-7.44 (m, 2H, CH arom), 8.36 (s, 1H, H-2). $^{13}$C NMR (MeOD) δ 14.4, 23.6, 27.7, 30.1, 32.6, 33.8, 43.7, 62.9, 72.6, 72.7, 87.5, 88.4, 128.0, 129.4, 130.0, 132.0, 139.4, 149.0, 151.0, 152.1, 155.0. HRMS (ESI) m/z Found: 474.2135 [M+H]$^+$, Calcd: 474.2175. Elem. anal. (C$_{23}$H$_{31}$N$_5$O$_4$S.0.25 CH$_2$Cl$_2$) C,H,N,S.

Example 7

6-benzyl-8-[(2-methyl-butyl)-amino]-thioinosine This compound was prepared according to general procedure D from 2',3',5'-tri-O-acetyl-6-benzyl-8-[(2-methyl-butyl)-amino]-thioinosine. Yield: 87%. White solid. M.p.: 129° C. $^1$H NMR (MeOD) δ 0.86-0.97 (m, 6H, 2×CH$_3$), 1.03-1.29 (m, 1H, CH$_3$CHH), 1.39-1.63 (m, 1H, CH$_3$CHH), 1.69-1.89 (m, 1H, CH$_3$CH), 3.13-3.50 (m, 2H, CH$_2$N), 3.73-3.82 (m, 2H, H-5'), 4.11-4.17 (m, 1H, H-4'), 4.25 (dd, 1H, J=1.5, J=5.5, H-3'), 4.61 (s, 2H, CH$_2$S), 4.67 (dd, 1H, J=5.5, J=7.7, (d, 1H, J=7.7, H-1'), 7.13-7.30 (m, 3H, CH arom), 7.40 (dd, 2H, J=1.8, J=7.7, CH arom), 8.36 (s, 1H, H-2). $^{13}$C NMR (MeOD) δ 11.5, 17.4, 27.9, 28.0, 33.9, 35.4, 62.9, 72.7, 72.8, 87.6, 88.3, 128.1, 129.4, 130.0, 132.1, 139.4, 149.0, 151.2, 152.0, 155.2. HRMS (ESI) m/z Found: 460.2013 [M+H]$^+$, Calcd: 460.2018. Elem. anal. (C$_{22}$H$_{29}$N$_5$O$_4$S.0.05 CH$_2$Cl$_2$) C,H,N,S.

Example 8

6-benzyl-8-(cyclopropylamino)-thioinosine This compound was prepared according to general procedure D from 2',3',5'-tri-O-acetyl-6-benzyl-8-(cyclopropylamino)-thioinosine. Yield: 58%. White solid. M.p.: 102° C. $^1$H NMR (MeOD) δ 0.56-0.66 (m, 2H, 2×CHH), 0.76-0.85 (m, 2H, 2×CHH), 2.78-2.90 (m, 2H, CH$_2$N), 3.72-3.88 (m, 2H, H-5'), 4.11 (dd, 1H, J=1.8, J=3.7, H-4'), 4.23 (dd, 1H, J=1.8, J=5.5, H-3'), 4.61 (dd, 1H, J=5.5, J=7.7, H-2'), 4.6 (s, 2H, CH$_2$S), 6.14 (d, 1H, J=7.7, H-1'), 7.15-7.32 (m, 3H, CH arom), 7.41-7.47 (m, 2H, CH arom), 8.41 (s, 1H, H-2). $^{13}$C NMR (MeOD) δ 7.0, 7.6, 25.5, 33.8, 62.9, 72.5, 72.7, 87.5, 88.4, 128.1, 129.4, 130.0, 131.7, 139.4, 149.3, 150.9, 152.8, 155.6. HRMS (ESI) m/z Found: 430.1497 [M+H]$^+$, Calcd: 430.1549. Elem. anal. (C$_{20}$H$_{23}$N$_5$O$_4$S.0.2 CH$_2$Cl$_2$) C,H,N,S.

Example 9

6-benzyl-8-(cyclopentylamino)-thioinosine This compound was prepared according to general procedure D from 2',3',5'-tri-O-acetyl-6-benzyl-8-(cyclopentylamino)-thioinosine. Yield: 80%. White solid. M.p.: 175-176° C. (dec.). $^1$H NMR (MeOD) δ 1.50-1.84 (m, 6H, 2×CH$_2$, 2×CHHCH), 1.94-2.13 (m, 2H, 2×CHHCH), 3.76-3.85 (m, 2H, H-5'), 4.12 (dd, 1H, J=1.8, J=3.7, H-4'), 4.25 (dd, 1H, J=1.8, J=5.5, H-3'), 4.29-4.44 (m, 1H, CHNH), 4.62 (s, 2H, CH$_2$S), 4.65 (dd, 1H, J=5.5, J=7.7, H-2'), 6.15 (d, 1H, J=7.7, H-1'), 7.15-7.32 (m, 3H, CH arom), 7.42 (dd, 2H, J=1.8, J=8.0, CH arom), 8.37 (s, 1H, H-2). $^{13}$C NMR (CDCl$_3$/MeOD 1/1) δ 24.6, 33.0, 33.1, 33.6, 55.1, 62.4, 72.0, 72.3, 86.9, 87.7, 127.7, 128.9, 130.0, 131.8, 138.4, 148.2, 150.2, 151.8, 154.1. HRMS (ESI) m/z Found: 458.1851 [M+H]$^+$, Calcd: 458.1862. Elem. anal. ($C_{22}H_{27}N_5O_4S$.0.05 $CH_2Cl_2$) C,H,N,S.

Example 10

6-benzyl-8-(cyclohexylamino)-thioinosine This compound was prepared according to general procedure D from 2′,3′,5′-tri-O-acetyl-6-benzyl-8-(cyclohexylamino)-thioinosine. Yield: 93%. White solid. M.p.: 108-109° C. $^1$H NMR (MeOD) δ 1.08-1.87 (m, 8H, 2×NHCHCHH, 3×CH$_2$), 1.93-2.09 (m, 2H, 2×NHCHCHH), 3.73-3.97 (m, 3H, H-5′, CH$_2$CHNH), 4.11-4.17 (m, 1H, H-4′), 4.26 (dd, 1H, J=1.8, J=5.8, H-3′), 4.61 (s, 2H, CH$_2$S), 4.67 (dd, 1H, J=5.8, J=7.7, H-2′), 6.14 (d, 1H, J=7.7, H-1′), 7.14-7.32 (m, 3H, CH arom), 7.38-7.44 (m, 2H, CH arom), 8.36 (s, 1H, H-2). $^{13}$C NMR (CDCl$_3$/MeOD 1/5, v/v) δ 26.3, 26.4, 26.5, 33.8, 33.9, 34.2, 53.2, 62.8, 72.5, 72.6, 87.4, 88.3, 128.0, 129.4, 130.0, 132.1, 139.3, 148.9, 151.0, 151.9, 154.4. HRMS (ESI) m/z Found: 472.1994. [M+H]$^+$, Calcd: 472.2018. Elem. anal. ($C_{22}H_{27}N_5O_4S$.0.25 $CH_2Cl_2$) C,H,N,S.

Example 11

6-benzyl-8-pyrrolidino-thioinosine This compound was prepared according to general procedure D from 2′,3′,5′-tri-O-acetyl-6-benzyl-8-pyrrolidino-thioinosine. Yield: 90%. White solid. M.p.: 158° C. (dec.). $^1$H NMR (CDCl$_3$/MeOD 1/9, v/v) δ 1.95-2.09 (m, 4H, 2×CH$_2$CH$_2$N), 3.66-3.80 (m, 5H, 2×CH$_2$N, 1×H-5′), 3.88 (ABX, 1H, J=2.6, J=12.4, 1×H-5′), 4.14 (dd, 1H, J=2.6, J=4.4, H-4′), 4.38 (dd, 1H, J=1.8, J=5.5, H-3′), 4.61 (s, 2H, CH$_2$S), 5.19 (dd, 1H, J=5.1, J=7.3, H-2′), 6.05 (d, 1H, J=7.3, H-1′), 7.21-7.32 (m, 3H, CH arom), 7.42 (dd, 2H, J=1.5, J=8.0, CH arom), 8.40 (s, 1H, H-2). $^{13}$C NMR (CDCl$_3$/MeOD 2/1, v/v) δ 26.1, 33.3, 51.6, 63.6, 72.1, 72.2, 87.2, 89.5, 127.5, 128.8, 129.4, 132.0, 138.0, 147.9, 149.3, 153.8, 156.3. HRMS (ESI) m/z Found: 444.1678 [M+H]$^+$, Calcd: 444.1705. Elem. anal. ($C_{21}H_{25}N_5O_4S$) C,H, N,S.

Example 12

6-benzyl-8-piperidino-thioinosine This compound was prepared according to general procedure D from 2′,3′,5′-tri-O-acetyl-6-benzyl-8-piperidino-thioinosine. Yield: 86%. Colorless glass. M.p.: 90-92° C. $^1$H NMR (CDCl$_3$/MeOD 1/9, v/v) δ 1.57-1.84 (m, 6H, 3×CH$_2$), 3.24-3.50 (m, 4H, 2×CH$_2$N), 3.80 (ABX, 1H, J=2.9, J=12.4, H-5′), 4.08-4.15 (m, 1H, H-4′), 4.40 (dd, 1H, J=2.2, J=5.5, H-3′), 4.61 (s, 2H, CH$_2$S), 5.19 (dd, 1H, J=5.5, J=7.3, H-2′), 5.81 (d, 1H, J=7.3, H-1′), 7.14-7.32 (m, 3H, CH arom), 7.37-7.46 (m, 2H, CH arom), 8.48 (s, 1H, H-2). $^{13}$C NMR (CDCl$_3$) δ 23.8, 25.1, 32.9, 52.1, 63.3, 72.1, 86.5, 89.0, 127.1, 128.3, 129.0, 130.2, 137.0, 147.9, 148.4, 156.4, 158.3. HRMS (ESI) m/z Found: 458.1834 [M+H]$^+$, Calcd: 458.1862. Elem. anal. ($C_{22}H_{27}N_5O_4S$.0.2 $CH_2Cl_2$) C,H,N,S.

Example 13

6-benzyl-8-morpholino-thioinosine This compound was prepared according to general procedure D from 2′,3′,5′-tri-O-acetyl-6-benzyl-8-morpholino-thioinosine. Yield: 94%. Colorless glass. M.p.: 98-99° C. $^1$H NMR (MeOD) δ 3.27-3.40 (m, 2H, CH$_2$N), 3.45-3.58 (m, 2H, CH$_2$N), 3.73 (ABX, 1H, J=2.9, J=12.4, H-5′), 3.81-3.94 (m, 5H, 2×CH$_2$O, 1×H-5′), 4.13 (dd, 1H, J=(dd, 1H, J=5.1, J=7.3, H-2′), 5.87 (d, 1H, J=7.3, H-1′), 7.14-7.33 (m, 3H, CH arom), 7.42 (dd, 2H, J=1.5, J=8.0, CH arom), 8.52 (s, 1H, H-2). $^{13}$C NMR (CDCl$_3$) δ 33.0, 51.3, 63.3, 66.0, 72.2, 72.5, 86.6, 88.7, 127.2, 128.4, 129.0, 130.2, 136.9, 147.9, 148.6, 157.2, 157.6. HRMS (ESI) mrz Found: 460.1625 [M+H]$^+$, Calcd: 460.1654. Elem. anal. ($C_{21}H_{25}N_5O_4S$.0.2 $CH_2Cl_2$) C,H,N,S.

9-benzyl-6-(4-nitrobenzylsulfanyl)-purine This compound was prepared according to a literature procedure (Tromp, R. A.; van Ameijde, S.; Pütz, C.; Sundermann, C.; Sundermann, B.; von Frijtag Drabbe Künel, J. K.; Ijzerman, A. P. Submitted for publication)

9-benzyl-6-chloropurine This compound was prepared according to a literature procedure (Kanie, K.; Mizuno, K.; Kuroboshi, M.; Hiyama, T. *Bull. Chem. Soc. Jpn.* 1998, 71, 1973-1991).

9-benzyl-hypoxanthine This compound was prepared according to a literature procedure (Maruyama, T.; Kozai, S.; Uchida, M. *Nucleosides & Nucleotides* 1999, 18, 661-671).

9-benzyl-8-bromo-hypoxanthine This compound was prepared according to a literature procedure.[11] After work-up the product was washed with CH$_2$Cl$_2$ and dried in vacuo to provide 62 as an off-white solid. Yield: 83%. White solid. $^1$H NMR (DMSO-d$_6$) δ 5.37 (s, 2H, CH$_2$N), 7.20-7.42 (m, 5H, CH arom), 8.11 (s, 1H, H-2), 12.53 (br s, 1H, NH). $^{13}$C NMR (DMSO-d$_6$) δ 42.7, 124.3, 125.5, 127.2, 128.9, 135.6, 146.7, 150.0, 155.4.

9-benzyl-8-(cyclopentylamine)-hypoxanthine This compound was prepared according to general procedure E. Yield: 67%. White solid. $^1$H NMR (DMSO-d$_6$) δ 1.43-1.96 (m, 8H, 4×CH$_2$), 4.06-4.19 (m, 1H, CHN), 5.22 (s, 2H, PhCH$_2$N), 6.46 (d, 1H, J=6.6, CHNH), 7.12-7.22 (m, 2H, CH arom), 7.24-7.38 (m, 3H, CH arom), 8.71 (s, 1H, H-2), 12.01 (br s, 1H, NH). $^{13}$C NMR (CDCl$_3$) δ 23.1, 33.0, 44.6, 54.3, 121.6, 126.8, 128.1, 128.9, 134.8, 142.3, 149.0, 151.3, 158.0.

9-benzyl-8-(cyclohexylamine)-hypoxanthine This compound was prepared according to general procedure E. Yield: 67%. Off-white solid. $^1$H NMR (CDCl$_3$) δ 0.96-2.03 (m, 10H, 5×CH$_2$), 3.79-4.02 (m, 2H, CHNH, NHCH), 5.18 (s, 2H, CH$_2$N), 7.18-7.43 (m, 5H, CH arom), 8.02 (s, 1H, H-2), 11.54 (br s, 1H, NH). $^{13}$C NMR (CDCl$_3$) δ 24.1, 24.8, 32.1, 43.4, 50.7, 120.8, 126.2, 127.1, 128.0, 134.8, 141.4, 148.0, 150.9, 155.8.

9-benzyl-8-pyrrolidino-hypoxanthine This compound was prepared according to general procedure A with omittance of the acetylation step (Yield: 74%) or general procedure E (Yield: 56%). White solid. $^1$H NMR (CDCl$_3$) δ 1.84-1.95 (m, 4H, 2×CH$_2$CH$_2$N), 3.50-3.62 (m, 4H, 2×CH$_2$N), 5.41 (s, 2H, CH$_2$N), 7.07-7.15 (m, 2H, CH arom), 7.25-7.39 (m, 3H, CH arom), 7.92 (s, 1H, H-2), 11.79 (br s, 1H, NH). $^{13}$C NMR (CDCl$_3$/MeOD 1/1, v/v) δ 24.7, 45.7, 49.0, 121.1, 125.1, 127.0, 128.2, 136.0, 141.9, 149.1, 152.8, 156.1.

9-benzyl-8-morpholino-hypoxanthine This compound was prepared according to general procedure A with omittance of the acetylation step (Yield: 55%) or general procedure E (Yield: 88%). White solid. $^1$H NMR (CDCl$_3$) δ 3.20 (t, 4H, J=4.7, 2×CH$_2$N), 3.76 (t, 4H, J=4.7, 2×CH$_2$O), 5.29 (s, 2H, CH$_2$N), 7.15-7.41 (m, 5H, CH arom), 8.01 (s, 1H, H-2), 11.72 (br s, 1H, NH). $^{13}$C NMR (CDCl$_3$/MeOD 4/1, v/v) δ 46.3, 50.3, 66.1, 121.4, 126.3, 127.8, 128.7, 135.4, 143.9, 149.4, 154.2, 157.4.

9-benzyl-8-(cyclopentylamine)-6-mercaptopurine This compound was prepared according to general procedure B. Yield: 8%. White solid. $^1$H NMR (CDCl$_3$/MeOD 3/1, v/v) δ 1.29-1.69 (m, 6H, 2×CHHCHNH, 2×CH$_2$), 4.32-4.52 (m, 1H, CHNH), 5.24 (s, 2H, CH$_2$N), 7.13-7.42 (m, 5H, CHarom), 7.98 (brs, 1H, H-2).

9-benzyl-8-(cyclohexylamine)-6-mercaptopurine This compound was prepared according to general procedure B. Yield: 44%. Pink solid. $^1$H NMR (CDCl$_3$/MeOD 1/1, v/v) δ

1.03-2.04 (m, 10H, 5×CH$_2$), 3.83-4.05 (m, 1H, NHCH), 5.27 (s, 2H, CH$_2$N), 7.12-7.39 (m, 5H, CH arom), 8.02 (s, 1H, H-2), 11.54 (br s, 1H, NH). $^{13}$C NMR (CDCl$_3$/MeOD 1/1, v/v) δ 24.1, 24.7, 32.2, 43.5, 50.6, 126.2, 127.3, 128.1, 134.0, 134.3, 141.5, 144.4, 152.6, 167.0.

9-benzyl-8-pyrrolidino-6-mercaptopurine This compound was prepared according to general procedure B. Yield: 53%. White solid. $^1$H NMR (CDCl$_3$/MeOD 5/1, v/v) δ 1.81-2.02 (m, 4H, 2×CH$_2$CH$_2$N), 3.55-3.72 (m, 4H, 2×CH$_2$N), 5.46 (s, 2H, CH$_2$N), 7.02-7.14 (m, 2H, CH arom), 7.27-7.40 (m, 3H, CH arom), 8.00 (s, 1H, H-2). $^{13}$C NMR (CDCl$_3$/MeOD 5/1, v/v) δ 25.1, 46.2, 49.6, 125.2, 127.5, 128.6, 134.2, 135.7, 141.7, 145.5, 154.3, 168.4.

9-benzyl-8-morpholino-6-mercaptopurine This compound was prepared according to general procedure B. Yield: 54%. Yellowish solid. $^1$H NMR (CDCl$_3$/MeOD 3/2, v/v) δ 3.23-3.31 (m, 4H, 2×CH$_2$N), 3.71-3.79 (m, 4H, 2×CH$_2$O), 5.32 (s, 2H, CH$_2$N), 7.14-7.22 (m, 2H, CH arom), 7.29-7.39 (m, 3H, CH arom), 8.02 (s, 1H, H-2). $^{13}$C NMR (DMSO-d$_6$) δ 46.0, 49.7, 65.5, 126.6, 127.6, 128.7, 133.0, 136.0, 144.2, 145.4, 155.3, 172.1.

Example 14

9-benzyl-8-(cyclopentylamine)-6-(4-nitrobenzyl)-mercaptopurine This compound was prepared according to general procedure C from 9-benzyl-8-(cyclopentylamine)-6-mercaptopurine. Yield: 21%. Yellow solid. M.p.: 150-151° C. $^1$H NMR (CDCl$_3$) δ 1.18-1.64 (m, 6H, 2×CH$_2$, 2×CHHCHNH), 1.89-2.08 (m, 2H, 2×CHHCHNH), 4.12 (d, 1H, J=7.3, CHNH), 4.25-4.42 (m, 1H, CHNH), 4.70 (s, 2H, CH$_2$S), 5.19 (s, 2H, CH$_2$N), 7.17 (dd, 2H, J=1.8, J=7.3, CH arom), 7.29-7.40 (m, 3H, CH arom), 7.64 (d, 2H, J=8.8, CH arom), 8.12 (d, 2H, J=8.8, CH arom), 8.51 (s, 1H, H-2). $^{13}$C NMR (CDCl$_3$) δ 23.2, 31.9, 33.2, 44.5, 54.4, 123.5, 127.0, 128.6, 129.3, 129.9, 131.0, 134.3, 146.6, 146.8, 148.7, 149.9, 150.3, 153.3. HRMS (ESI) m/z Found: 461.1736 [M+H]$^+$, Calcd: 461.1754.

Example 15

9-benzyl-8-(cyclohexylamine)-6-(4-nitrobenzyl)-mercaptopurine This compound was prepared according to general procedure C from 9-benzyl-8-(cyclohexylamine)-6-mercaptopurine. Yield: 19%. Yellow solid. M.p.: 66-68° C. $^1$H NMR (CDCl$_3$) δ 0.96-1.64 (m, 8H, 3×CH$_2$, 2×CHHCHNH), 1.83-1.97 (m, 2H, 2×CHHCHNH), 3.82-4.01 (m, 1H, NHCH), 4.08 (d, 1H, J=8.0, CHNH), 4.70 (s, 2H, CH$_2$S), 5.20 (s, 2H, CH$_2$N), 7.12-7.24 (m, 2H, CH arom), 7.28-7.42 (m, 3H, CH arom), 7.64 (d, 2H, J=8.8, CH arom), 8.13 (d, 2H, J=8.8, CH arom), 8.51 (s, 1H, H-2). $^{13}$C NMR (CDCl$_3$) δ 24.2, 25.3, 31.8, 32.9, 44.5, 50.9, 123.5, 126.9, 128.5, 129.2, 129.9, 134.3, 146.6, 146.8, 148.6, 149.7, 150.2, 153.0. HRMS (ESI) m/z Found: 475.1955 [M+H]$^+$, Calcd: 475.1911. Elem. anal. (C$_{25}$H$_{26}$N$_6$O$_2$S.0.3CH$_2$Cl$_2$) C,H,N,S.

Example 16

9-benzyl-6-(4-nitrobenzyl)-8-pyrrolidino-mercaptopurine This compound was prepared according to general procedure C from 9-benzyl-8-pyrrolidino-6-mercaptopurine. Yield: 83%. Yellow solid. M.p.: 154° C. $^1$H NMR (CDCl$_3$) δ 1.85-1.93 (m, 4H, 2×CH$_2$CH$_2$N), 3.56-3.63 (m, 4H, 2×CH$_2$CH$_2$N), 4.71 (s, 2H, CH$_2$S), 5.46 (s, 2H, CH$_2$N), 7.02-7.09 (m, 2H, CH arom), 7.24-7.37 (m, 3H, CH arom), 7.65 (d, 2H, J=8.8, CH arom), 8.13 (d, 2H, J=8.8, CH arom), 8.50 (s, 1H, H-2). $^{13}$C NMR (CDCl$_3$) δ 25.1, 31.6, 46.1, 49.2, 123.2, 125.2, 127.5, 128.6, 129.7, 130.5, 135.9, 146.3, 146.5, 148.2, 149.6, 151.1, 154.6. HRMS (ESI) m/z Found: 447.1594 [M+H]$^+$, Calcd: 447.1598. Elem. anal. (C$_{23}$H$_{22}$N$_6$O$_2$S.0.2CH$_2$Cl$_2$) C,H,N,S.

Example 17

9-benzyl-8-morpholino-6-(4-nitrobenzyl)-mercaptopurine This compound was prepared according to general procedure C from 9-benzyl-8-morpholino-6-mercaptopurine. Yield: 78%. White solid. M.p.: 201° C. $^1$H NMR (Bruker DMX 600 MHz, DMSO-d$_6$, 60° C.) δ 3.28 (t, 4H, J=4.8, 2×CH$_2$N), 3.63 (t, 4H, J=4.8, 2×CH$_2$O), 4.77 (s, 2H, CH$_2$S), 5.38 (s, 2H, CH$_2$N), 7.17-7.19 (m, 2H, CH arom), 7.26-7.34 (m, 3H, CH arom), 7.74 (d, 2H, J=8.8, CH arom), 8.15 (d, 2H, J=8.8, CH arom), 8.57 (s, 1H, H-2). $^{13}$C NMR (Bruker DMX 600 MHz, DMSO-d$_6$, 60° C.) δ 30.7, 46.1, 49.0, 65.2, 123.1, 126.4, 127.3, 128.4, 129.2, 129.8, 135.7, 146.3, 146.5, 149.5, 150.8, 152.0, 156.2. HRMS (ESI) m/z Found: 463.1583 [M+H]$^+$, Calcd: 463.1547. Elem. anal. (C$_{23}$H$_{22}$N$_6$O$_3$S.0.1CH$_2$Cl$_2$) C,H,N,S.

Example 18

6 (benzo[c][1,2,5]oxadiazole-5-ylmethylsulfanyl)-9-benzyl-8-pyrrolidin-1-yl-9H-purine This compound was prepared according to general procedure C from the respective thiol. Yield: 72%. Yellowish solid. $^1$H NMR (CDCl$_3$) δ=1.84-1.97 (m, 4H, 2×CH$_2$CH$_2$N), 3.54-3.67 (m, 4H, 2×CH$_2$N), 4.61 (s, 2H, CH$_2$S), 5.47 (s, 2H, CH$_2$N), 7.01-7.10 (m, 2H, CH arom), 7.23-7.37 (m, 3H, CH arom), 7.55 (dd, 1H, J=1.5, J=9.1, CH arom), 7.75 (d, 1H, J=9.1, CH arom), 7.89 (s, 1H, CH arom), 8.52 (s, 1H, H-2). $^{13}$C NMR (CDCl$_3$) δ=25.5, 32.4, 46.3, 49.6, 114.7, 116.2, 125.6, 127.7, 128.9, 134.1, 136.4, 142.7, 148.7, 149.2, 151.7, 154.9, 158.8. Elem. anal. (C$_{23}$H$_{21}$N$_7$OS.0.1CH$_2$Cl$_2$) C,H,N,S.

Example 19

6-(benzo[c][1,2,5]oxadiazole-5-ylmethylsulfanyl)-9-benzyl-8-morpholin-4-yl-9H-purine This compound was prepared according to general procedure C from the respective thiol. Yield: 48%. White solid. $^1$H NMR (CDCl$_3$MeOD 9/1, v/v) δ=3.29 (t, 4H, J=4.8, 2×CH$_2$), 3.73 (t, 4H, J=4.8, 2×CH$_2$), 4.72 (s, 2H, CH$_2$S), 5.32 (s, 2H-1, PhCH$_2$N), 7.11-7.36 (m, 5H, CH Ph), 7.54 (dd, 1H, J=1.1, J=9.1, CH Ph), 7.77 (d, 1H, J=9.1, CH Ph), 7.91 (d, 1H, J=1.1, CH Ph), 8.62 (s, 1H, H-2). $^{13}$C NMR (CDCl$_3$/MeOD 2/1, v/v) δ=32.0, 46.5, 49.4, 65.7, 114.3, 115.8, 126.0, 127.6, 128.6, 133.8, 134.8, 142.2, 148.1, 149.8. HRMS (ESI) m/z Found: 460.1536 [M+H]$^+$, Calcd: 460.1550. Elem. anal. (C$_{23}$H$_{21}$N$_7$O$_2$S.0.2 CH$_2$Cl$_2$) C,H,N,S.

Example 20

9-benzyl-6-benzylsulfanyl-8-morpholin-4-yl-9H-purine This compound was prepared according to general procedure C from 9-benzyl-8-morpholino-6-mercaptopurine. Yield: 78%.—Colorless oil.—$^1$H NMR (CDCl$_3$) δ=3.27 (t, 4H, J=4.8, 2×CH$_2$N), 3.72 (t, 4H, J=4.8, 2×CH$_2$O), 4.66 (s, 2H, CH$_2$S), 5.31 (s, 2H, PhCH$_2$N), 7.14-7.38 (m, 8H, CH Ph), 7.46 (m, 2H, CH Ph), 8.63 (s, 1H, H-2). —$^{13}$C NMR (CDCl$_3$) δ=32.8, 46.7, 49.9, 66.1, 126.4, 127.1, 127.9, 128.4, 128.9, 129.1, 129.6, 135.5, 137.6, 150.4, 150.7, 155.2, 156.4.

Example 21

9-benzyl-6-benzylsulfanyl-8-pyrrolidin-1-yl-9H-purine

This compound was prepared according to general procedure C from 9-benzyl-8-pyrrolidino-6-mercaptopurine. Yield: 48%.—Colorless glass.—$^1$H NMR (CDCl$_3$) δ=1.83-1.95 (m, 4H, 2×CH$_2$CH$_2$N), 3.52-3.68 (m, 4H, 2×CH$_2$N), 4.67 (s, 2H, CH$_2$S), 5.45 (s, 2H, CH$_2$N), 7.02-7.10 (m, 2H, CH arom), 7.21-7.39 (m, 6H, CH arom), 7.43-7.52 (m, 2H, CH arom), 8.52 (s, 1H, H-2). —$^{13}$C NMR (CDCl$_3$) δ=25.5, 32.9, 46.3, 49.5, 125.7, 127.0, 127.6, 128.3, 128.8, 129.1, 136.5, 137.9, 148.8, 151.3, 151.5, 154.8, 158.5. HRMS (ESI) m/z Found: 402.1726 [M+H]$^+$, Calcd: 402.1746. Elem. anal. (C$_{23}$H$_{23}$N$_5$S.0.15 CH$_2$Cl$_2$) C,H,N,S.

Assay

All final products according to Examples 1-17 were tested in the following radioligandbinding assay. Human erythrocyte membranes were used as a rich source of the nuleoside transport protein with [$^{3H}$]NBTI as the radioligand (K$_D$ value: 0.59±0.07 nM).

100 ml compound or buffer
100 ml [$^3$H]NBTI 1.5 nM
100 ml buffer (50 mM Tris.HCl, pH 7.4)
100 ml erythrocyte membranes After 30' incubation at 25° C.:
filtration over Whatman GF/C filters (50 mM Tris.HCl used for washing)
filters in vials
3.5 ml scintillation fluid
counting in beta counter after 2 hours Data:

| Example | Binding Nucleoside Transporter (Ki) [nM] |
|---|---|
| 1 | 28 |
| 2 | 9.5 |
| 3 | 5.3 |
| 4 | 5.4 |
| 5 | 2.3 |
| 6 | 3.7 |
| 7 | 3.6 |
| 8 | 3.0 |
| 9 | 0.64 |
| 10 | 0.94 |
| 11 | 410 |
| 12 | 744 |
| 13 | 33%$^c$ |
| 14 | 29 |
| 15 | 55 |
| 16 | 1519 |
| 17 | 51 |
| 18 | 43% |
| 19 | 122 |
| 20 | 1389 |
| 21 | 514 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to Formula I:

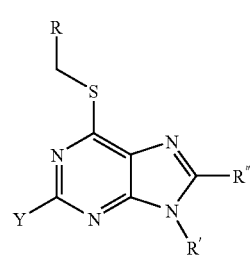

wherein

Y is selected from the group consisting of H, OH, SH, F, Cl, Br, I, —CF$_3$, —CHF$_2$, —CH$_2$F, —OCH$_3$, —OC$_2$H$_5$, —CH$_3$ and —C$_2$H$_5$;

R is selected from the group consisting of phenyl, benzyl, heteroaryl, and bicyclic fused ring structures composed of a benzo ring and a heteroaryl ring, each unsubstituted or mono- or polysubstituted with at least one substituent selected from the group consisting of R$^{23}$, OR$^{23}$, halogen, CF$_3$, CN, NO$_2$, NR$^{24}$R$^{25}$, C$_{1-6}$-alkyl, C$_{1-6}$-alkoxy, C$_{3-8}$-cycloalkoxy, saturated or mono- or poly-unsaturated but not aromatic C$_{3-8}$-cycloalkyl and C$_{2-6}$-alkylene, respectively;

R' is selected from the group consisting of C$_{1-6}$-alkyl, each saturated or unsaturated, and unsubstituted or mono- or polysubstituted with at least one substituent selected from the group consisting of halogen, NH$_2$, SH and OH; saturated or mono- or poly-unsaturated but not aromatic C$_{3-8}$-cycloalkyl and saturated C$_{3-8}$-cycloalkyl containing 1 or 2 heteroatoms selected from the group consisting of S, O and N in the ring, each unsubstituted or mono- or polysubstituted with at least one substituent selected from the group consisting of R$^{23}$, OR$^{23}$, halogen, CF$_3$, CN, NO$_2$, NR$^{24}$R$^{25}$, C$_{1-6}$-alkyl, C$_{1-6}$-alkoxy, C$_{3-8}$-cycloalkoxy, saturated or mono- or poly-unsaturated but not aromatic C$_{3-8}$-cycloalkyl and C$_{2-6}$-alkylene, respectively; phenyl and benzyl, each unsubstituted or mono- or polysubstituted with at least one substituent selected from the group consisting of R$^{23}$, OR$^{23}$, halogen, CF$_3$, CN, NO$_2$, NR$^{24}$R$^{25}$, C$_{1-6}$-alkyl, C$_{1-6}$-alkoxy, C$_{3-8}$-cycloalkoxy, saturated or mono- or poly-unsaturated but not aromatic C$_{3-8}$-cycloalkyl and C$_{2-6}$-alkylene, respectively; and C$_{1-6}$-alkyl-O—R''', wherein the alkyl may be saturated or unsaturated, and unsubstituted or mono- or polysubstituted with at least one substituent selected from the group consisting of halogen, NH$_2$, SH and OH, and R''' is selected from the group consisting of phenyl, heteroaryl, saturated or mono- or poly-unsaturated but not aromatic C$_{3-8}$-cycloalkyl, saturated C$_{3-8}$-cycloalkyl containing 1 or 2 heteroatoms selected from the group consisting of S, O and N in the ring, each unsubstituted or mono- or polysubstituted with at least one substituent selected from the group consisting of R$^{23}$, OR$^{23}$, halogen, CF$_3$, CN, NO$_2$, NR$^{24}$R$^{25}$, C$_{1-6}$-alkyl, C$_{1-6}$-alkoxy, C$_{3-8}$-cycloalkoxy, saturated or mono- or poly-unsaturated but not aromatic C$_{3-8}$-cycloalkyl and C$_{2-6}$-alkylene, respectively; and R" is selected from the group consisting of NH—C$_{1-6}$-alkyl, NH-aryl, NH-heteroaryl, NH—C$_{3-8}$-cycloalkyl wherein C3-8-cycloalkyl may be saturated or mono- or poly-unsaturated but not aromatic, NH—C$_{1-3}$-alkylaryl, NH—$C_{1-3}$-alkyl-heteroaryl, N($C_{1-6}$-alkyl)$_2$, N($C_{1-3}$-alkyl-aryl)$_2$, N($C_{1-3}$-alkyl-heteroaryl)$_2$, piperidino, piperazino, morpholino and pyrrolidino, each unsubstituted or mono- or polysubstituted with at least one substituent selected from the group consisting of $R^{23}$, $OR^{23}$, halogen, $CF_3$, CN, $NO_2$, $NR^{24}R^{25}$, $C_{1-6}$-alkyl, $C_{1-6}$-alkoxy, $C_{3-8}$-cycloalkoxy, saturated or mono- or poly-unsaturated but not aromatic $C_{3-8}$-cycloalkyl and $C_{2-6}$-alkylene, respectively;

where
$R^{23}$ denotes H, $C_{1-10}$-alkyl, aryl, heteroaryl, or an aryl or heteroaryl group bonded via a $C_{1-3}$-alkylene group; and
$R^{24}$ and $R^{25}$ are identical or different and denote H, $C_{1-10}$-alkyl, aryl, heteroaryl or an aryl or heteroaryl group bonded via a $C_{1-3}$-alkylene group, or $R^{24}$ and $R^{25}$ together denote $CH_2CH_2OCH_2CH_2$, $CH_2CH_2NR^{26}CH_2CH_2$, or $(CH_2)_{3-6}$, where $R^{26}$ denotes H, $C_{1-10}$-alkyl, aryl, heteroaryl, or an aryl or heteroaryl group bonded via a $C_{1-3}$-alkylene group; and
wherein "alkyl" means a saturated or unsaturated, branched or unbranched hydrocarbon chain;
or a salt thereof;
in the form of a pure stereoisomer or a mixture of stereoisomers in any mixing ratio.

2. A compound according to claim 1, in the form of a pure enantiomer or pure diastereoisomer.

3. A compound according to claim 1, in the form of a racemic mixture.

4. A compound according to claim 1, in the form of a physiologically compatible acid addition salt thereof.

5. A compound according to claim 1, wherein R is selected from the group consisting of phenyl, benzyl, and phenyl condensed with a heteroaryl, each unsubstituted or mono or disubstituted with substituents selected from the group consisting of OH, F, Cl, Br, I, —$CF_3$, —$OCH_3$, —$OC_2H_5$, —$CH_3$ and —$C_2H_5$.

6. A compound according to claim 1, wherein R is selected from the group consisting of 4-nitrophenyl, benzo[c][1,2,5]oxadiazole, and unsubstituted phenyl.

7. A compound according to claim 1, wherein R' is selected from the group consisting of n-butyl; 4-hydroxy-butyl; cyclopentyl; tetrahydrofuranyl; tetrahydropyranyl; benzyl unsubstituted or mono- or disubstituted with $NO_2$, F, phenyl, I, Cl, trifluoromethoxy, trifluoromethyl or methoxy; and -butyl-O-tetrahydropyranyl.

8. A compound according to claim 7, wherein R' is benzyl.

9. A compound according to claim 1, wherein R" is selected from the group consisting of NH—$C_{1-6}$-alkyl, NH—$C_{3-8}$-cycloalkyl, N($C_{1-6}$-alkyl)$_2$, piperidino, morpholino and pyrrolidino, each unsubstituted or mono- or polysubstituted, respectively.

10. A compound according to claim 9, wherein R" is selected from the group consisting of NH—$C_{1-6}$-alkyl, NH—$C_{3-6}$-cycloalkyl, piperidino, morpholino and pyrrolidino.

11. A compound according to claim 1, wherein Y denotes hydrogen.

12. A compound according to claim 1, selected from the group consisting of:
9-benzyl-8-(cyclopentylamine)-6-(4-nitrobenzyl)-mercaptopurine; 9-benzyl-8-(cyclohexylamine)-6-(4-nitrobenzyl)-mercaptopurine;
9-benzyl-6-(4-nitrobenzyl)-8-pyrrolidino-mercaptopurine; 9-Benzyl-8-morpholino-6-(4-nitrobenzyl)-mercaptopurine;
6-(benzo[c][1,2,5]oxadiazole-5-ylmethylsulfanyl)-9-benzyl-8-pyrrolidin-1-yl-9H-purine;
6-(benzo[c][1,2,5]oxadiazole-5-ylmethylsulfanyl)-9-benzyl-8-morpholin-4-yl-9H-purine;
9-benzyl-6-benzylsulfanyl-8-morpholin-4-yl-9H-purine; and 9-benzyl-6-benzylsulfanyl-8-pyrrolidin-1-yl-9H-purine.

13. A pharmaceutical composition comprising a compound according to claim 1, and at least one pharmaceutical carrier or auxiliary material.

14. A method of treating pain in a patient in need thereof, said method comprising administering to said patient an effective pain alleviating amount of a compound according to claim 1.

15. A method according to claim 14, wherein said pain is neuropathic pain.

* * * * *